(12) United States Patent
Yoshida et al.

(10) Patent No.: US 7,217,548 B2
(45) Date of Patent: May 15, 2007

(54) N-ACETYLGLUCOSAMINLYTRANSFERASE AND POLYNUCLEOTIDE ENCODING THE SAME

(75) Inventors: Aruto Yoshida, Kanagawa (JP); Makoto Takeuchi, deceased, late of Kanagawa (JP); by Yoriko Takeuchi, legal representative, Kanagawa (JP); Tamao Endo, Tokyo (JP); Hiroshi Manya, Tokyo (JP); Yasunori Chiba, Ibaraki (JP); Yoshifumi Jigami, Ibaraki (JP); Shigemi Sugioka, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 365 days.

(21) Appl. No.: 10/398,523

(22) PCT Filed: Oct. 5, 2001

(86) PCT No.: PCT/JP01/08833

§ 371 (c)(1),
(2), (4) Date: Sep. 15, 2003

(87) PCT Pub. No.: WO02/31159

PCT Pub. Date: Apr. 18, 2002

(65) Prior Publication Data

US 2004/0132130 A1    Jul. 8, 2004

(30) Foreign Application Priority Data

Oct. 6, 2000    (JP)    ............................. 2000-307435

(51) Int. Cl.
*C12P 21/06*    (2006.01)
*C12N 9/10*    (2006.01)
*C12N 1/00*    (2006.01)
*C12N 15/00*    (2006.01)
*C07H 21/04*    (2006.01)

(52) U.S. Cl. ................. 435/193; 435/193; 435/254.11; 435/154.2; 435/320.1; 435/69.1; 435/252.3; 536/23.2; 536/23.5

(58) Field of Classification Search ............... 536/23.1; 435/320.1, 254.11, 183, 91.1, 68.1; 535/397; 424/94.1

See application file for complete search history.

(56) References Cited

U.S. PATENT DOCUMENTS 6,558,935 B1 *    5/2003    Tang et al. ................. 435/193

2002/0192752 A1 *    12/2002    Goddard et al. ........... 435/69.1
2003/0004311 A1 *    1/2003    Baker et al. ................. 530/350
2003/0073129 A1 *    4/2003    Baker et al. ................. 435/7.1

FOREIGN PATENT DOCUMENTS

| WO | WO 00/12708 A2 | 3/2000 |
|----|----|----|
| WO | WO 00/14251 A2 | 3/2000 |
| WO | WO 00/14251 A2 | 3/2000 |
| WO | WO200014251 A2 * | 3/2000 |
| WO | WO 00/12708 A2 | 9/2000 |

OTHER PUBLICATIONS

Gleeson et al., Control of glycoprotein synthesis. JBC., 258(10): 6162-6173, 1983.*
Kumar et al., Cloning and expression of N-acetylglucosaminyltransferase I, the medial golgi transferase that initiates complex N-linked carbohydrate formation. PNAS., 87:9948-9952, 1990.*
Lussier et al., The Ktr1p, Ktr3p, and Kre2/Mnt1p mannosyltransferases participate in the elaboration of yeast O- and N-linked carbohydrate chains. JBC., 1997, vol. 272 (24): 15527-15531.*
Database GenBank, AK000284, Sugano et al., *Homo sapiens* cDNA FLJ20277 fis, clone HEP02567, 22 Feb. 22, 2000.
Kumar et al., "Cloning and expression of N-acetylglucosaminyltransfersae I, the medial Golgi transferas that initiates complex N-linked carbohydrate formation", *Pro. Nalt. Acad. Sci. USA.*, Dec. 1990, pp. 9948-9952, vol. 87.
Takahashi et al., "A new β-1, 2-N-acetylglucosaminyltransferas that may play a role in the biosynthesis of mammalin O-mannosyl glycans", *Glycobiology*, 2001, pp. 37-45, vol. 11, No. 1, Oxford University Press.
Yoshida et al., "Muscular Dystrophy and Neuronal Migration Disorder Caused by Mutations in a Glycosyltransferase, POMGnT1", *Developmental Cell*, Nov. 2001, pp. 717-724, vol. 1, Cell Press.

* cited by examiner

*Primary Examiner*—Rebecca E. Prouty
*Assistant Examiner*—Ganapathirama Raghu
(74) *Attorney, Agent, or Firm*—Foley & Lardner LLP

(57) ABSTRACT

The present invention relates to an enzyme having novel N-acetylglucosaminyltransferase (OMGnT) activity, a polynucleotide encoding the enzyme, a recombinant polynucleotide comprising the polynucleotide, a host cell comprising the recombinant polynucleotide, a method for producing an enzyme protein having OMGnT activity by culturing the host cell in a medium, and a method for modifying a sugar chain structure with the enzyme and a carbohydrate having a sugar chain structure modified by the method. This enzyme enables the production of complex carbohydrates, which could not be formed with conventional glycosyltransferases.

8 Claims, 6 Drawing Sheets

N-ACETYLGLUCOSAMINLYTRANSFERASE AND POLYNUCLEOTIDE ENCODING THE SAME

FIELD OF THE INVENTION

The present invention relates to a novel N-acetylglucosaminyltransferase (OMGnT) enzyme protein which recognizes a specific sugar chain structure in a complex carbohydrate and introduces thereinto a GlcNAcβ1→2Man structure, an activity assay method and production method for the protein, and polynucleotides encoding the protein. Further, the present invention relates to cells having the polynucleotides introduced thereinto, a production method of sugar chains and carbohydrates (glycosylated amino acids, glycopeptides, glycoproteins, and derivatives thereof) using the same, and the produced sugar chains and carbohydrates (glycosylated amino acids, glycopeptides, glycoproteins, and derivatives thereof).

BACKGROUND OF THE INVENTION

1. Glycoprotein O-Linked Man Type Sugar Chain

Among proteins derived from eukaryotes, glycoproteins modified with sugar chains are frequently found rather than simple proteins composed of only amino acids. It is known that these sugar chains are responsible for the stability of proteins or the maintenance of tertiary structure, or they play important roles in intermolecular recognition for intercellular adhesion, etc. Major sugar chains of glycoproteins include the N-linked type binding to asparagine and O-linked type binding to serine (Ser) or threonine (Thr) (Makoto Takeuchi, Glycobiology Series 5, Glycotechnology, edited by Akira Kihata, Sen-ichiro Hakomori, and Katsutaka Nagai, Kodansha Scientific, 191–208 (1994)). In all the cases regarding N-linked type, N-acetylglucosamine (GlcNAc) is bound to an amide group of asparagine. On the other hand, regarding O-linked type, there exist several different kinds which have different sugars bound to the hydroxyl groups of Ser or Thr. Among these, a series of sugar chains in which mannose is bound to the amino acid are classified as the O-linked Man type. In addition to this, mucin type in which N-acetylgalactosamine (GalNAc) is bound and O-linked GlcNAc type in which N-acetylglucosamine (GlcNAc) is bound are widely known. These O-linked type sugar chains differ not only in sugars bound to amino acids but also in their entire sugar chain structures [Van den Steen, P., Rudd, P. M., Dwek, R. A., and Opdenakker, G, Crit. Rev. Biochem. Mol. Biol., (1998), 33, 151–208].

O-linked Man type sugar chains are often found in glycoproteins of yeasts, fungi, or the like. In the case of yeasts, most constituent sugars are mannose, but there are some known cases wherein a small number of phosphates or galactoses (Gal) are bound thereto. The structure of sugar chains is not-uniform and varies depending on the type of yeast. For example, a structure having 7 sugars or less, wherein 1 to 3 residues of mannose are linearly bound to a protein and additional mannose, galactose, or mannose phosphate is transferred thereto [Gemmill, T. R. and Trimble, R. B., Biochim. Biophys. Acta, (1999), 1426, 227–237].

Regarding sugar chain biosynthesis, researches have been made with a focus on baker's yeasts (*Saccharomyces cerevisiae*, hereinafter referred to as *S. cerevisiae*), and the biosynthesis is considered to proceed along the pathway as shown in FIG. 1. First, a reaction occurs wherein mannose is transferred via α-linkage to a hydroxide group of Ser or Thr with a protein O-mannosyltransferase (PMTp) [Strahl-Bolsinger, S., Gentzsch, M., and Tanner, W., Biochim. Biophys. Acta, (1999), 1426, 297–307]. Further, another mannose is bound via α-1,2 linkage with any one of KRE2p, KTR1p, and KTR3p, thereby forming a structure having 2 residues of mannose bound. When KRE2p acts on this sugar chain continuously, the structure having 3 residues of mannose bound via α-1,2 linkage is formed [Lussier, M., Sdicu, A. M., Bussereau, F., Jacquet, M., and Bussey, H., J. Biol. Chem., (1997), 272, 15527–15531]. The subsequent biosynthesis pathway is divided into two: one path wherein further 1 to 2 residues of mannose are bound thereto via α-1,3 linkage with MNN1p, MNT2p, and MNT3p [Romero, P. A., Lussier, M., Veronneau, S., Sdicu, A. M., Herscovics, A., and Bussey, H., Glycobiology, (1999), 9, 1045–1051]; and the other path wherein mannose phosphate is transferred with MNN6p [Jars, M. U., Osborn, S., Forstrom, J., and MacKay, V. L., J. Biol. Chem., (1995), 270, 24810–24817]. Meanwhile, when mannose is transferred via α-1,3 linkage, mannose phosphate transfer reaction is inhibited [Nakayama, K., Feng, Y., Tanaka, A., and Jigami, Y., Biochim. Biophys. Acta, (1998), 1425, 255–262]

In contrast, animal O-linked Man type sugar chains had been virtually unknown, but in recent years there have been reports thereon one after another. First, NeuAcα2→3Galβ1→4GlcNAcβ1→2Manα1→Ser/Thr structure was discovered from α-dystroglycan of bovine peripheral nerve [Chiba, A., Matsumura, K., Yamada, H., Inazu, T., Shimizu, T., Kusunoki, S., Kanazawa, I., Kobata, A., and Endo, T., J. Biol. Chem., (1997), 272, 2156–2162]. Thereafter, the existence of similar sugar chain structures in α-dystroglycan derived from rabbit skeletal muscles or sheep brains was confirmed [Sasaki, T., Yamada, H., Matsumura, K., Shimizu, T., Kobata, A., and Endo, T., Biochem. Biophys. Acta, (1998), 1425, 599–606, Smalheiser, N. R., Haslam, S. M., Sutton-Smith, M., Morris, H. R., and Dell, A., J. Biol. Chem., (1998), 273, 23698–23703]. Further, from rabbit brain extract, $HSO_3$→3GlcAβ1→3Galβ1→4GlcNAcβ1→2Manα1→Ser/Thr structure which contains HNK-1 epitope that is considered to play an important role in constructing neural circuits, was reported [Yuen, C.-T., Chai, W., Loveless, R. W., Lawson, A. M., Margolis, T., and Feizi, T., J. Biol. Chem., (1997), 272, 8924–8931]. According to these reports, it is clear that O-linked Man type sugar chain also exists in animals. However, animal sugar chains have sialic acid (NeuAc), galactose, N-acetylglucosamine, glucuronic acid (GlcA), and sulfate groups bound thereto, and thus they are quite different in structure from those known in yeasts or fungi.

Biosynthesis pathway of O-linked Man type sugar chains in animals have hardly been learned. Regarding an enzyme that transfers mannose to a protein, a homolog of yeast PMT gene has been obtained, but its function has not been confirmed [Perez Jurado, L. A., Coloma, A., and Cruces, J., Genomics, (1999), 58, 171–180]. In addition, it has been discovered that the gene mutation which causes rotated abdomen in *Drosophila* occurs in a gene having a high homology with a yeast PMT gene [Martin-Blanco, E. and Garcia-Bellido, A., Proc. Natl. Acad. Sci. USA, (1996), 93, 6048–6052]. However, it is not clear whether this gene has PMT activity or not. Further, the enzymes which are engaged in the elongation of O-linked Man type sugar chain, such as the enzyme (OMGnT) that transfers β 1,2-linked N-acetylglucosamine to mannose which is bound to a protein, are not well-understood.

2. Function of O-Linked Man Type Sugar Chain

*S. cerevisiae* has 7 types of PMTp isozymes as enzymes to transfer mannose to proteins. Among these, the disruption of 3 genes (PMT1, PMT2, and PMT4 or PMT2, PMT3, and PMT4) disables its growth [Strahl-Bolsinger, S., Gentzsch, M., and Tanner, W., Biochim. Biophys. Acta, (1999), 1426, 297–307]. Further, the mutation of *Drosophila rt* gene, which has a high homology with the PMT gene of yeast, is a cause for morphological abnormalities [Martin-Blanco, E. and Garcia-Bellido, A., Proc. Natl. Acad. Sci. USA, (1996), 93, 6048–6052]. Therefore, there is considered to be a possibility that O-linked Man type sugar chains of proteins have important roles in the growth and morphogenesis of organisms.

It has been known that an O-linked Man type sugar chain is bound to α-dystroglycan in animals [Endo, T., Biochim. Biophys. Acta, (1999), 1473, 237–246]. α-dystroglycan along with β-dystroglycan is a glycoprotein encoded by a dystroglycan gene, and, through posttranslational cleavage, two components, α and β are formed [Ibraghimov-Beskrovnaya, O., Ervasti, J. M., Leveille, C. J., Salughter, C. A., Sernett, S. W., and Campbell, K. P., Nature, (1992), 355, 696–702]. Both of them are expressed in the basal membrane of nerve tissues or muscles, and α-dystroglycan exists with binding to an extracellular domain of β-dystroglycan which is a transmembrane protein. Further, α-dystroglycan is extracellularly bound to laminin-1, laminin-2, agrin, or other extracellular matrices, and β-dystroglycan is intracellularly bound to dystrophin or other similar cytoskeletal proteins. Therefore, α- and β-dystroglycans are assumed to play roles in joining a cytoskeleton to an extracellular matrices [Henry, M. D. and Campbell, K. P., Curr. Opin. Cell Biol., (1999), 11, 602–607]. This complicated structure wherein such a plurality of molecules are bound together is referred to as a dystrophin glycoprotein complex (DGC), and its close relation to the morphogenesis of organisms has been proven. For example, gene abnormalities of any component of dystrophin [Koenig, M., Hoffman, E. P., Bertelson, C. J., Monaco, A. P., Feener, C., and Kunkel, L. M., Cell, (1987), 50, 509–517], laminin-2 [Xu, H., Wu, X. R., Wewer, U. M., and Engval, E., Nature Genet., (1994), 8, 297–302] and dystroglycan [Cote, P. D., Moukhles, H., Lindenbaum, M., and Carbonetto, S., Nature Genet., (1999), 23, 338–342] cause muscular dystrophy which is a serious disease.

It is indicated that, in the linkage between α-dystroglycan and laminin in a DGC, a 3'-sialyl N-acetyllactosamine (NeuAcα2→3Galβ1→4GlcNAc) structure of the O-linked type sugar chain existing in α-dystroglycan is important [Chiba, A., Matsumura, K., Yamada, H., Inazu, T., Shimizu, T., Kusunoki, S., Kanazawa, I., Kobata, A., and Endo, T., J. Biol. Chem., (1997), 272, 2156–2162]. This sugar chain structure is substantially recognized in O-linked Man type sugar chains of skeletal muscle-derived α-dystroglycan [Sasaki, T., Yamada, H., Matsumura, K., Shimizu, T., Kobata, A., and Endo, T., Biochim. Biophys. Acta, (1998), 1425, 599–606]. Thus, there is a high likelihood that O-linked Man type sugar chains have an important role in the linkage of α-dystroglycan and laminin. If it is true, a mutation of OMGnT that is essential to the biosynthesis of this sugar chain is presumed to cause abnormalities in the DGC structure, and furthermore it is considered that OMGnT is likely to be a causative gene for yet to be elucidated muscular dystrophy-like nervous diseases or morphological abnormalities.

Accordingly, the use of antibodies/antiserum obtained by using OMGnT protein of the present invention as antigens, or the use of all or a part of the polynucleotide encoding OMGnT of the present invention as a probe is useful for the detection and genetic diagnosis of lesions, or the like caused by the above-mentioned muscular dystrophy-like nervous diseases or morphological abnormalities.

It is reported that α-dystroglycan is involved in the infection of peripheral nerve Schwann cells with the bacteria, *Mycobacterium leprae* (hereinafter, referred to as *M.leprae*), which is known to be a cause of Hansen's disease [Rambukkana, A., Yamada, H., Zanazzi, G., Mathus, T., Salzer, J. L., Yurchenco, P. D., Campbell, K. P., and Fischetti, V. A., Science, (1998), 282, 2076–2079]. The authors revealed that *M. leprae* is bound to the G domain of the laminin-2 α2 chain (LNα2G) that is normally bound to α-dystroglycan specifically, and selectively infects peripheral nerves. Further, *M. leprae* is bound via LNα2G to α-dystroglycan prepared from peripheral nerve or skeletal muscle, though such linkage is not observed in the case of recombinant α-dystroglycan prepared from *E. coli*, indicating that the α-dystroglycan sugar chain is an important element in the infectivity of *M. leprae*.

Moreover, it is revealed that α-dystroglycan is an infection target of pathogenic viruses such as Arena viruses including the Lassa fever virus, or Lymphocytic choriomeningitis virus [Cao, W., Henry, M. D., Borrow, P., Yamada, H., Elder, J. H., Ravkov, E. V., Nichol, S. T., Compans, R. W., Campbell, K. P., and Oldstone, B. A., Science, (1998), 282, 2079–2081]. In this case, the virus is bound to α-dystroglycans derived from rabbit skeletal muscle, but not to recombinant α-dystroglycans produced by *E. coli*, indicating that the α-dystroglycan sugar chain has an important role in infection. Further, the virus is not bound to the α2 subunit of a dihydropyridine receptor complex which is a glycoprotein likewise derived from rabbit skeletal muscle. Therefore, it is pointed out that the sugar chain structure specifically bound to α-dystroglycan is important in the infection. Accordingly, it is considered that there is an extremely high possibility that the very rarely observed O-linked Man type sugar chain is a target of the virus.

As described above, there is a high likelihood that O-linked Man type sugar chains of α-dystroglycan are extensively involved in the infection of pathogenic bacteria or viruses. Hence, when a carbohydrate containing O-linked Man type sugar chain is administered to an organism, it is expected to suppress the binding of bacteria or virus to α-dystroglycan. This action is useful in preventing the infectivity of the above-mentioned pathogenic bacteria or viruses, or to cure infected patients and stop the deterioration of symptoms. However, in order to implement these events, large volumes of carbohydrates containing O-linked Man type sugar chains are necessary, and the use of OMGnT of the present invention for the synthesis of the carbohydrate enables this implementation. In addition, among host cells having polynucleotides encoding OMGnT introduced therein, for example, yeast cells (the details are described below), are useful since they can produce human-type O-linked Man type sugar chains at low cost.

3. Production of Mammal-Derived Glycoproteins in Yeast

Various yeasts as typified by *S. cerevisiae* are often used as hosts to conduct mass production of recombinant proteins. Most physiologically active mammalian proteins are obtained from living bodies usually only in extremely small amounts, and thus if inexpensive mass production of recombinant proteins with yeast is possible, this would be very useful. However, mammalian proteins are bound to sugar chains in most cases, and their structure is largely different from that of yeasts. Thus, it is often the case that the proteins simply expressed in yeasts cannot be used as pharmaceuticals [Romanos, M. A., Scorer, C. A., and Clare, J. J., Yeast, (1992), 8, 423–488, Eckart, M. R. and Bussineau, C. M., Curr. Opin. Biotechnol., (1996), 7, 525–530]. Particularly, the fact that Manα1→3Manα1→2 structure contained in yeast sugar chains has antigenicity to humans is a major problem [Young, M., Davies, M. J., Bailey, D., Gradwell, M. J., Smestad-Paulsen, B., Wold, J. K., Barnes, R. M. R., and Hounsell, E. F., Glycoconj. J., (1998), 15, 815–822].

In order to overcome these problems, in recent years, technologies to convert a yeast sugar chain structures to those similar to mammals' have been in the process of development. For example, a technology to convert yeast N-linked type sugar chain to an animal sugar chain structure has been already established [Chiba, Y., Suzuki, M., Yoshida, S., Yoshida, A., Ikenaga, H., Takeuchi, M., Jigami, Y., and Ichishima, E., J. Biol. Chem., (1998), 273, 26298–26304]. As for O-linked type sugar chain, the other major sugar chain, however, there has not been such an idea nor technology. If a technology to convert O-linked type sugar chain to a sugar chain structure similar to mammals' is established, it is considered that together with the conversion technologies for N-linked type sugar chains, problems concerning almost all the sugar chains would be solved.

4. N-acetylglucosaminyltransferase (GnT)

There have been no reports on an enzyme (OMGnT) which transfers N-acetylglucosamine via β1,2 linkage to mannose bound to serine or threonine in a protein. However, as the enzyme N-acetylglucosaminyltransferase (GnT) which transfers N-acetylglucosamine to mannose, GnT-I, GnT-II, GnT-III, GnT-IV, GnT-V, and GnT-VI have been reported [Schachter, H., Brockhausen, I., and Hull, E., Methods Enzymol., (1989), 179, 351–397]. All of these are involved in the biosynthesis of N-glycan, and each recognizes their intrinsic substrates for transfer reaction. Hitherto, cDNA cloning has been carried out for the following: GnT-I [Kumar, R., Yang, J., Larsen, R. D. and Stanley P., Proc. Natl. Acad. Sci. USA, (1990), 87, 9948–9952, Sarkar, M., Hull, E., Nishikawa, Y., Simpson, R. J., Moritz, R. L., Dunn, R., and Schachter, H., Proc. Natl. Acad. Sci. USA, (1991), 88, 234–238]; GnT-II [D'Agostaro, G A., Zingoni, A., Moritz, R L., Simpson, R J., Schachter, H. and Bendiak, B., J. Biol. Chem., (1995), 270, 15211–15221]; GnT-III [Nishikawa, A., Ihara, Y., Hatakeyama, M., Kangawa, K. and Taniguchi, N., J. Biol. Chem., (1992), 267, 18199–18204]; GnT-IV; and GnT-V [Shorebah, M. G., Hindsgaul, O. and Pierce, M., J. Biol. Chem., (1992), 267, 2920–2927]. With respect to GnT-IV, the existence of the following two isozymes has been revealed: -IVa [Yoshida, A., Minowa, M. T., Takamatsu, S., Hara, T., Oguri, S., Ikenaga, H. and Takeuchi, M., Glycobiology, (1999), 9, 303–310] and -IVb [Yoshida, A., Minowa, M. T., Takamatsu, S., Hara, T., Ikenaga, H. and Takeuchi, M., Glycoconj. J., (1998), 15, 1115–1123]. Among these, 62% amino acid sequence identity has been recognized between human GnT-IVa and GnT-IVb, which have the same enzymatic activity. However, although they catalyze similar enzymatic reactions, there exists no clear homology between GnT-I and GnT-II that transfer GlcNAc via β1,2 linkage to mannose, or between GnT-III and GnT-IV that transfer GlcNAc via β1,4 linkage to mannose. Further, any significant homology cannot be found between GnTs which differ in transfer manner of GlcNAc. From these findings, it is generally considered that there is no sequence homology among various GnTs which transfer N-acetylglucosamine to mannose.

Herein, "identity" is an expression illustrating the degree of identical individual amino acid residues constituting sequences. In this case, the expression includes a case wherein alignment processing is performed in consideration of the existence of a gap. Further, "homology" used herein is an expression whose scope includes the scope of the above "identity" and further similar amino acid usage (e.g., isoleucine and leucine, and asparagine and glutamic acid), and the like.

An object of the present invention is to provide: a protein (enzyme) having novel N-acetylglucosaminyltransferase (hereinafter referred to as OMGnT) activity; a polynucleotide encoding the above enzyme; a recombinant polynucleotide containing the above polynucleotide; cells of mammals, yeasts, or the like containing the above recombinant polynucleotide; a method for producing an enzyme protein having OMGnT activity by cultivating the cells in a medium and the enzyme protein produced by the method; a method for producing a novel substance using OMGnT; a method for producing O-linked Man type sugar chains and carbohydrates (glycosylated amino acids, glycopeptides, glycoproteins, and derivatives thereof) by culturing cells having the above polynucleotides introduced thereinto in a medium; and O-linked Man type sugar chains and carbohydrates (glycosylated amino acids, glycopeptides, glycoproteins, and derivatives thereof) produced by the above method.

SUMMARY OF THE INVENTION

The present inventors have made intensive research to solve the above problems, and have succeeded in the cloning of OMGnT cDNA from human brain-derived RNA. Then, by confirming that this cDNA encoding product exhibits OMGnT activity, the inventors have completed the present invention.

Namely, the present invention provides the following (1) to (22):

(1) A N-acetylglucosaminyltransferase having an activity to produce a carbohydrate having a partial structure represented by the following formula:

using UDP-GlcNAc and a complex carbohydrate having a partial structure represented by the following formula:

as substrates, wherein the UDP-GlcNAc is a sugar donor and the complex carbohydrate is a sugar receptor.

(2) The N-acetylglucosaminyltransferase according to above (1), wherein the sugar receptor is a glycosylated amino acid, a glycopeptide, or a glycoprotein, or a derivative thereof.

(3) A N-acetylglucosaminyltransferase having an activity to produce a carbohydrate (a glycosylated amino acid, a glycopeptide, a glycoprotein, and a derivative thereof) which has a partial structure represented by the following formula:

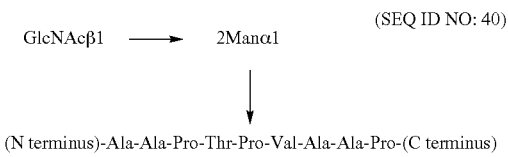

using UDP-GlcNAc and a complex carbohydrate having a partial structure represented by the following formula:

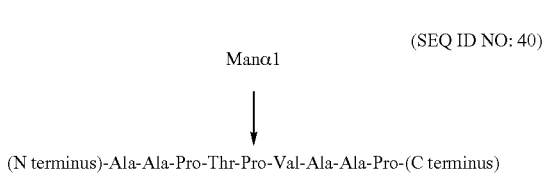

as substrates, wherein the UDP-GlcNAc is a sugar donor and the complex carbohydrate is a sugar receptor.

(4) The N-acetylglucosaminyltransferase according to any of (1) to (3) above, wherein a divalent cation is required for its activity.

(5) A protein having an amino acid sequence shown in SEQ ID NO:2.

(6) A protein having an amino acid sequence comprising at least from position 247:Ser to position 660:Thr of the amino acid sequence shown in SEQ ID NO:2.

(7) A protein having an amino acid sequence comprising addition, deletion, insertion, and/or substitution of one or more amino acids to the amino acid sequence comprising at least from position 247:Ser to position 660:Thr of the amino acid sequence shown in SEQ ID NO:2, and having N-acetylglucosaminyltransferase activity according to any of (1) to (4) above.

(8) A polynucleotide encoding N-acetylglucosaminyltransferase according to any one of (5) to (7) above.

(9) A polynucleotide encoding N-acetylglucosaminyltransferase comprising a nucleotide sequence shown in SEQ ID NO:1.

(10) A recombinant polynucleotide obtained by insertion of a polynucleotide encoding N-acetylglucosaminyltransferase according to (8) or (9) above into a vector.

(11) A host cell comprising the recombinant polynucleotide according to (10) above.

(12) A yeast cell comprising the recombinant polynucleotide according to (10) above and having at least one of KRE2, (SEQ ID NO: 41), KTR1(SEQ ID NO: 42), and KTR3 (SEQ ID NO: 43) genes disrupted.

(13) A yeast cell comprising the recombinant polynucleotide according to (10) above and being a triple disrupted strain wherein KRE2, (SEQ ID NO: 41) KTR1 (SEQ ID NO: 42), and KTR3 (SEQ ID NO: 43) genes are disrupted.

(14) A method for producing N-acetylglucosaminyltransferase comprising the step of collecting a protein having N-acetylglucosaminyltransferase activity according to any of (1) to (4) above from a biological sample.

(15) A method for producing N-acetylglucosaminyltransferase comprising the steps of: culturing the cell according to any of (11) to (13) above in a medium; and collecting a protein having N-acetylglucosaminyltransferase activity from cultured cell or culture medium.

(16) A method for producing a sugar chain or a carbohydrate having a modified sugar chain structure, comprising the steps of: culturing the cell according to any of (11) to (13) above; centrifuging and disrupting cultured cell; and obtaining the sugar chain or the carbohydrate having the modified sugar chain structure.

(17) A method for assaying N-acetylglucosaminyltransferase activity comprising the step of: separating and detecting by a reverse phase HPLC a glycopeptide represented by the following formula:

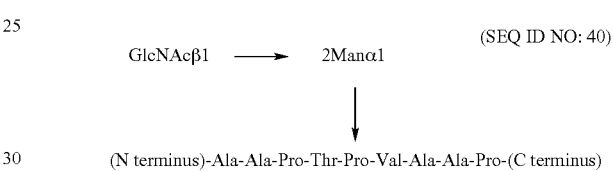

using UDP-[³H]GlcNAc and a complex carbohydrate having a partial structure represented by the following formula:

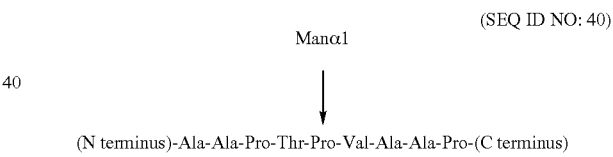

as substrates, wherein the UDP-[³H]GlcNAc is a sugar donor and the complex carbohydrate is a sugar receptor.

(18) A yeast cell retaining the protein according to any one of (5) to (7) above.

(19) The yeast cell according to (18) above, further retaining a UDP-GlcNAc transporter.

(20) The yeast cell according to (18) or (19) above comprising the recombinant polynucleotide according to (10) above, wherein 1 to 3 genes of KRE2 (SEQ ID NO: 41), KTR1 (SEQ ID NO: 42), and KTR3 (SEQ ID NO: 43) genes are disrupted.

(21) A method for producing a sugar chain or a carbohydrate having a modified sugar chain structure, comprising the steps of: culturing the yeast cell according to any one of (18) to (20) above; centrifuging and disrupting cultured cell; and obtaining the sugar chain and the carbohydrate having the modified sugar chain structure.

(22) The method according to (21) above, wherein the sugar chain modification is a conversion of an O-linked Man type sugar chain to a mammal type GlcNAcβ1→2Man structure.

Panel A shows a pattern when transfer reaction was brought about with the addition of a microsomal fraction derived from a rat brain to a reaction solution, and Panel B shows a pattern without the addition thereof. The elution position of Man-peptide to which [$^3$H]GlcNAc was transferred is indicated by an arrow in Panel A. A dotted line indicates a concentration gradient (%) of acetonitrile.

Figure 3:
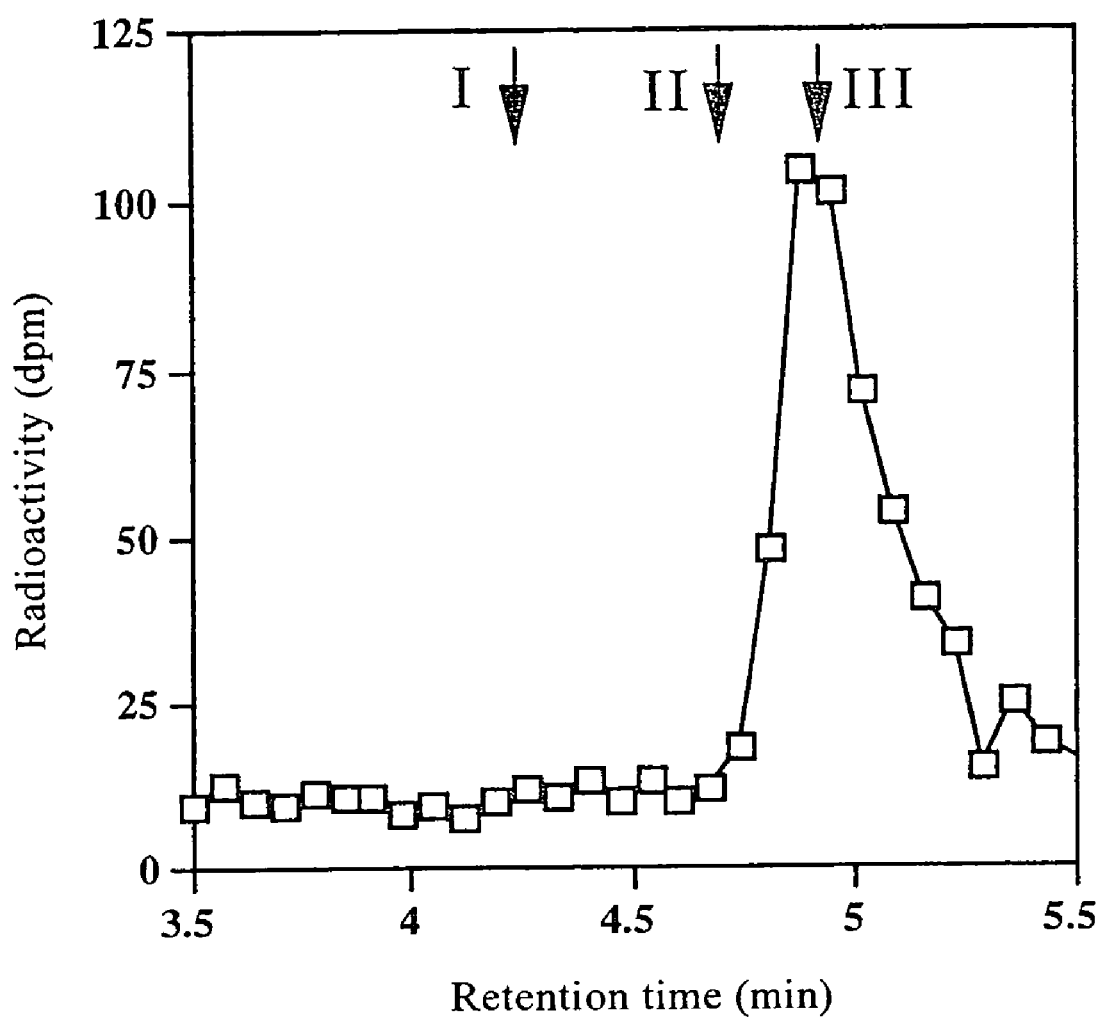

FIG. 3 shows sugar chain structure analysis of an OMGnT reaction product by HPAEC-PAD.

In the figure, arrows I, II, and III indicate the elution positions of GlcNAcβ1→6Man$_{OH}$, GlcNAcβ1→4Man$_{OH}$ and GlcNAcβ1→3Man$_{OH}$, and GlcNAcβ1→2Man$_{OH}$, respectively.

Figure 4:
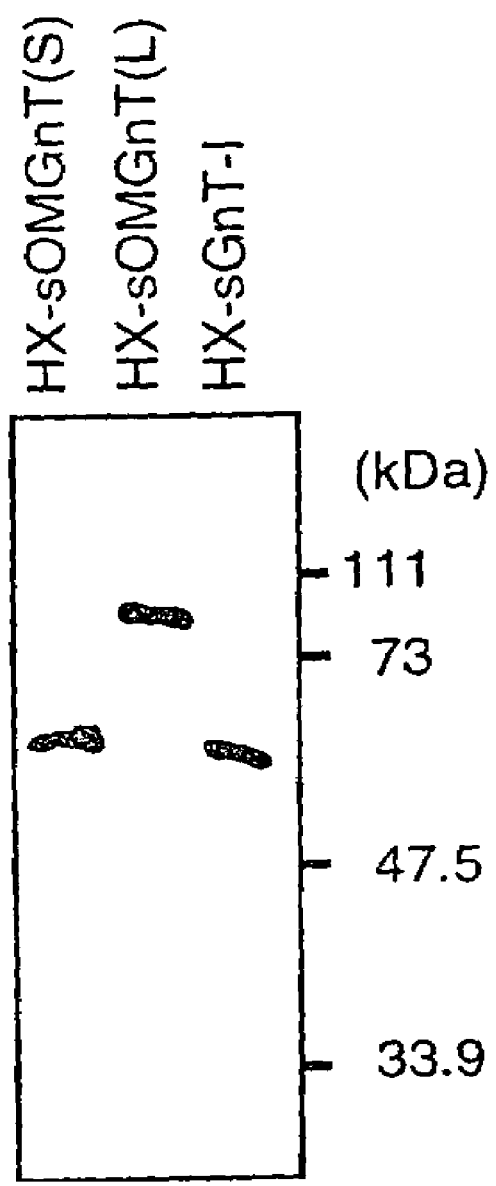

FIG. 4 shows Western blot analysis on His-Xpress-sOMGnT(S), His-Xpress-sOMGnT(L), and His-Xpress-sGnT-I, which are solubilized enzymes expressed in animal cells.

Figure 5:
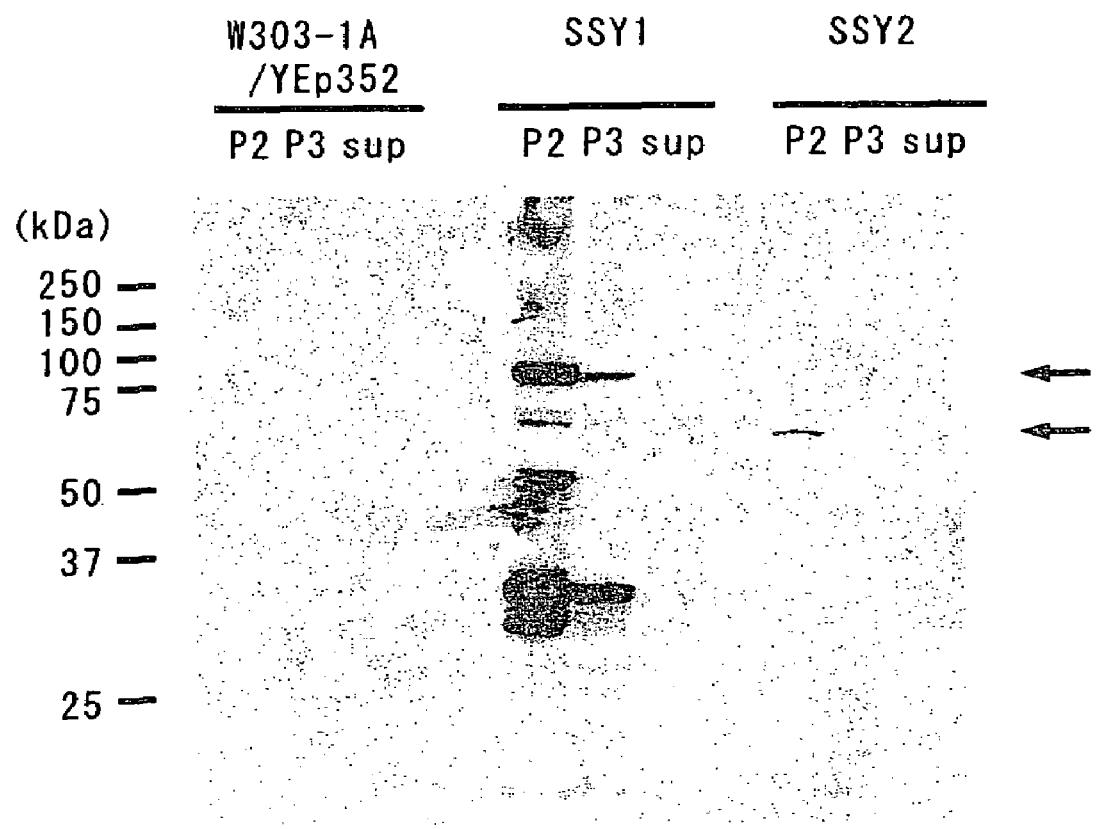

FIG. 5 shows Western blot analysis on membrane-linked type OMGnT and OCH1-OMGnT, both being expressed in yeast cells. P2, P3 and sup in the figure represent precipitated fractions obtained by centrifugation at 10,000×g and 100,000×g, and a supernatant fraction obtained by centrifugation at 100,000×g, respectively. The position for each expression of membrane-linked OMGnT and OCH1-OMGnT is indicated by an arrow.

Figure 6:
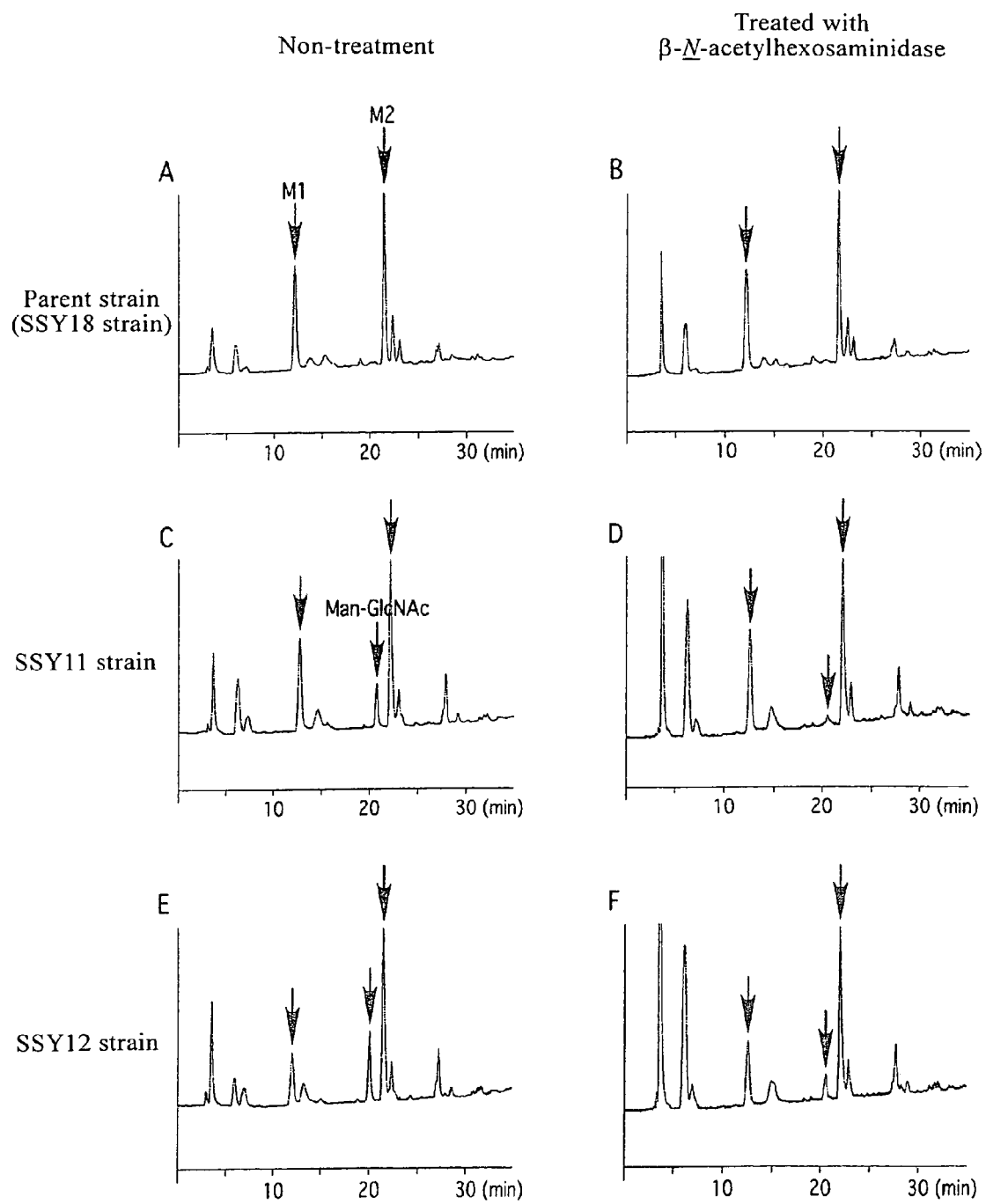

FIG. 6 shows sugar chain structure analysis of O-linked type sugar chain obtained from mannoprotein on yeast cell surface by a normal phase HPLC. Panel A shows the result of sugar chain structure analysis of a parent strain (SSY18), and Panel B shows the result of the treated sugar chain of the parent strain with β-N-acetylhexosamimidase. Panel C shows the result of sugar chain structure analysis of a strain (SSY11) to which a gene encoding membrane-linked type OMGnT was introduced, and Panel D shows the result of the treated sugar chain of the strain with β-N-acetylhexosamimidase. Panel E shows the result of sugar chain structure analysis of a strain (SSY12) to which a gene encoding membrane-linked type OCH1-OMGnT was introduced, and Panel F shows the result of the treated sugar chain of the strain with β-N-acetylhexosamimidase.

DETAILED DESCRIPTION OF THE INVENTION

Hereinafter, the present invention will be described in detail.

The polynucleotide encoding OMGnT of the present ivention can be isolated as described below.

DNA database, GenBank, is searched using BLAST for an EST (expression sequence tag) clone encoding a gene for a protein having an amino acid sequence similar to that of human GnT-I. As a result, a clone exhibiting high similarity is obtained, and based on the information on nucleotide sequence of the clone, primer DNAs can be prepared. Then, RT-PCR using RNA extracted from a human tissue (e.g., brain) and 5'-RACE using cDNA prepared from a human tissue can be performed to amplify a partial fragment of OMGnT cDNA. The nucleotide sequence of the amplified partial cDNA can be analyzed by inserting it into a plasmid vector, for example, pCR-TOPO 2.1 (Invitrogen). Integration of the information concerning these nucleotide sequences can determine the entire nucleotide sequence of cDNA encoding human OMGnT. Next, the amino acid sequence of OMGnT polypeptide encoded by this cDNA can be determined. The thus obtained cDNA sequence and amino acid sequence of human OMGnT are as shown in SEQ ID NOS: 1 and 2, respectively. The cDNA encoding human OMGnT can be prepared by ligating the obtained partial fragments with each other. Further, the cDNA encoding human OMGnT can be obtained by preparing primer DNAs based on the nucleotide sequence information of human OMGnT, and conducting RT-PCR with RNA extracted from a human tissue (e.g., brain).

To obtain a polynucleotide encoding a sequence comprising addition, deletion, insertion, and/or substitution of one or more amino acids in the amino acid sequence as shown in SEQ ID NO: 2 or an amino acid sequence from position 247:Ser to position 660:Thr of the amino acid sequence as shown in SEQ ID NO: 2, several methods can be employed. Examples of such include: a method of mutagen-treatment on polynucleotides to cause point mutations or deletion mutations; a method comprising the steps of selectively cleaving a gene, removing or adding a selected nucleotide therefrom or thereto, and ligating fragments of the gene; and the oligonucleotide mutagenesis method [Sambrook, J, Fritsch, E. F., and Maniatis, T., Molecular Cloning: A Laboratory Manual, 2nd Ed., Cold Spring Harbor Laboratory, Cold Spring Harbor, N.Y. (1989), 15.3–15.113]. When OMGnT mutants obtained by expressing polynucleotides prepared by the above methods exhibit the activity, they can be used in the same manner as the polynucleotide encoding OMGnT disclosed in the present invention.

Herein, the number of mutations (addition, deletion, insertion, and/or substitution) in the amino acid sequence of SEQ ID NO: 2 is described as "one or more," but the number is not particularly limited. The number is at least 1 to 30, preferably 1 to 20, more preferably 1 to several, or 1 to 10, and most preferable 1 to 3.

The number of these mutations is allowed to be any number as long as the mutants substantially exhibit OMGnT activity. Further, the polynucleotide of the present invention encompasses a nucleotide sequence encoding a protein having at least 80% or more, preferably 90% or more, more preferably 95% or more, most preferably 97% or more homology to the amino acid sequence as shown in SEQ ID NO: 2. The homology figures used herein are computed as positives using, for example, BLAST.

Further, in addition to the polynucleotide encoding N-acetylglucosaminyltransferase having a nucleotide sequence as shown in SEQ ID NO: 1, the nucleotide of the present invention includes polynucleotide sequences obtained by hybridization with all or a part of the nucleotide sequence of SEQ ID NO: 1 under stringent conditions. The stringent conditions described herein means that, for example, the sodium concentration is 10 to 300 mM, preferably 20 to 100 mM, and the temperature is 25 to 70° C., preferably 42 to 55° C. In general, it is known that a lower ionic strength and/or a higher temperature can lead to enhanced stringency. In the case where the hybridization is first conducted under low stringent or medium stringent conditions, and thereafter washing is conducted under high stringent conditions, high stringency can be implemented. The hybridization conditions are described in, for example, F. M. Ausubel et al., Protocols in Molecular Biology (John Wiley & Sons), and reference to this can be made.

Obtained by the above method, the polynucleotide encoding the OMGnT of the present invention can be inserted into the downstream of a promoter in a suitable vector to prepare a recombinant vector, the recombinant vector can be introduced into a host cell, and the obtained cells can be cultured, thereby producing OMGnT of the present invention. Examples of the promoter used herein include promoters derived from human cytomegalovirus and promoters derived from simian virus 40. The vector to be used may be a plasmid or a bacteriophage. For example, a vector: pcDNA3.1 (Invitrogen), which will be described later in the Examples, may be used. Further, OMGnT is inherently a transmembrane protein, and thus the deletion of the transmembrane region at the N-terminus thereof and the expression of replaced protein with a secretory signal of Ig kappa chain enable the extracellular production of solubilized enzyme. As host cells to which the recombinant polynucleotides are introduced, as long as cells can be used for gene recombination technologies, any cell can be used, such as prokaryotic cells, eukaryotic cells (animal cells, yeast cells, fungal cells, insect cells, etc.). For example, the following cells may be used: E. coli as prokaryotic cells; and mammalian cells as animal cells among eukaryotic cells, such as HEK293 cells derived from human embryonic kidney, CHO cells derived from Chinese hamster ovary, and COS cells derived from African Green Monkey kidney.

The transformation may be carried out by methods commonly used for each host. For example, when the host is E. coli, competent cells are prepared by the calcium chloride method or other methods, and then vectors containing the recombinant polynucleotides can be introduced into the competent cells by the thermal shock method or electroporation [Sambrook, J, Fritsch, E. F., and Maniatis, T., Molecular Cloning: A Laboratory Manual, 2nd Ed., Cold Spring Harbor Laboratory, Cold Spring Harbor, N.Y. (1989), 1.74–1.85]. When the hosts are yeast cells, competent cells are prepared by lithium chloride method or other methods, and then vectors containing the recombinant polynucleotides can be introduced into the competent cells by thermal shock method or electroporation [Becker, D. M. and Guarente, L., Methods Enzymol., (1991), 194, 182–187]. When the hosts are animal cells, vectors containing the recombinant polynucleotides can be introduced into cells in growth phase or the like by calcium phosphate method, lipofection, or electroporation [Sambrook, J, Fritsch, E. F., and Maniatis, T., Molecular Cloning: A Laboratory Manual, 2nd Ed., Cold Spring Harbor Laboratory, Cold Spring Harbor, N.Y. (1989), 16.30–16.55].

The thus obtained transformants are cultured in a medium, thereby allowing them to produce OMGnT proteins. In culturing the transformants, the medium to be used for the cultivation may be any medium as long as the medium is one which enables each host to grow. For example, when the host is E. coli, LB medium or the like may be used. When the host is yeast, YPD medium or the like may be used. When the host is an animal cell, Dulbecco's MEM supplemented with animal serum, or the like may be used. The cultivation is carried out under the conditions commonly used for each host. For example, when E. coli is used as host, the cultivation is carried out at approximately 30 to 37° C. for approximately 3 to 24 hours, and if necessary aeration or stirring may be additionally conducted. When yeast is used as host, the cultivation is carried out at approximately 25 to 37° C. for approximately 12 hours to 2 weeks and if necessary aeration or stirring may be additionally conducted. When animal cells are used as host, the cultivation is carried out at approximately 32 to 37° C. for approximately 24 hours to 2 weeks under the conditions of 5% $CO_2$, 100% humidity, and if necessary the air phase condition may be changed or stirring may be additionally conducted.

After cultivation, the cultured cell bodies or cells are disrupted either by a homogenizer, a French press, ultrasound, lysozyme, and/or freeze thawing. OMGnT proteins are eluted from cell bodies, and then the proteins can be obtained from a soluble fraction. Additionally, when the protein of interest is contained in an insoluble fraction, other methods may be used, wherein the insoluble fraction after cell bodies or cells are disrupted, is collected by centrifugation and the insoluble fraction is changed to a soluble one with a buffer solution containing guanidine hydrochloride, or the like so as to collect the protein. Besides these methods, a method wherein cell bodies or cells are directly disrupted with a buffer solution containing a protein denaturant such as guanidine hydrochloride to elute the protein of interest extracellularly.

The purification of OMGnT protein from the above supernatant can be conducted by any suitable combination of separation/purification methods well known in the art. Examples of these methods include centrifugation, salt precipitation, solvent precipitation, dialysis, ultrafiltration, partition chromatography, gel filtration, gel electrophoresis, capillary electrophoresis, TLC, ion exchange chromatography, metal chelate chromatography, affinity chromatography, reverse phase chromatography, and isoelectric focusing.

The biochemical properties of the OMGnT: an enzyme protein massively expressed in animal cells as described above are as follows.

(1) Action

This enzyme produces a carbohydrate having a partial structure represented by the formula below:

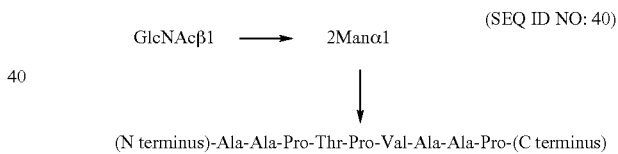

using UDP-GlcNAc and a complex carbohydrate having a partial structure represented by the following formula:

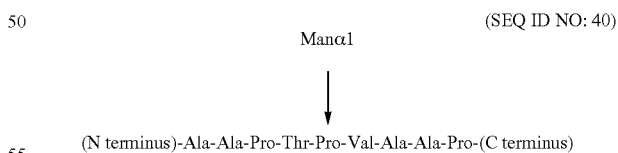

as substrates, wherein the UDP-GlcNAc is a sugar donor and the complex carbohydrate is a sugar receptor.

The complex carbohydrate, as the sugar receptor, refers to a glycosylated amino acid, a glycopeptide, a glycoprotein, and a derivative (carbohydrate) thereof.

(2) Substrate Specificity

When the carbohydrate, as the sugar receptor, is mannosylnanopeptide and the reactivity of the enzyme is regarded as 100%, the enzyme protein exhibits a reactivity of 0% toward mannose and p-nitrophenyl mannose. Further, the enzyme protein exhibits 0% reactivity toward GnT-I substrates.

(3) Molecular Weight

From the nucleotide sequence of the cDNA, OMGnT is considered to be a protein consisting of 660 amino acid residues with a molecular weight of approximately 71.5 K. However, a protein consisting of 414 amino acid residues at C-terminal side with a molecular weight of approximately 51.6 K is sufficient for OMGnT activity.

(4) Requisite for Divalent Cation

Divalent cations are essential for activity expression. Among divalent cations, $Mn^{2+}$ exhibits the maximum effect. $Mg^{2+}$ exhibits approximately 40% and $Ca^{2+}$ exhibits approximately 15% of the effect of $Mn^{2+}$, at a concentration of 10 mM for each divalent cation. The effect of $Mn^{2+}$ is the greatest at the concentration range of 1 to 10 mM.

(5) Kinetic Parameters

Under assay conditions in which the enzyme is reacted in 125 mM MOPS buffer (pH7.3) containing 0.4 mM Man-peptide, 7.5 mM $MnCl_2$, 200 mM GlcNAc, 0.5%(w/v) Triton X-100, 10% glycerol, and 1% BSA at 37° C. for 2 hours, the apparent Km value of His-Xpress-sOMGnT (L) toward UDP-GlcNAc is 0.73 mM. On the other hand, under the same assay conditions except for the inclusion of 0.2 mM UDP-GlcNAc, Km value of His-Xpress-sOMGnT(L) toward Man-peptide is 1.85 mM. The apparent Km value of His-Xpress-sOMGnT(S) toward UDP-GlcNAc and Km value thereof toward Man-peptide are 0.57 and 1.36 mM, respectively.

(6) Homology to Other Proteins

The protein encoded by human OMGnT polynucleotide of the present invention has 24.4% amino acid sequence identity to human GnT-I protein. However, OMGnT does not have GnT-I activity, and GnT-I does not have OMGnT activity, either. Further, OMGnT composed of 660 amino acids has more amino acid residues by 115 amino acids longer than GnT-I which is composed of 445 amino acids, and particularly the N-terminal region of OMGnT is longer, which makes them quite different.

From the biochemical properties described above, the OMGnT of the present invention was recognized as a novel glycosyltransferase in the point that it is able to perform the following reaction which conventional glycosyltransferases cannot perform:

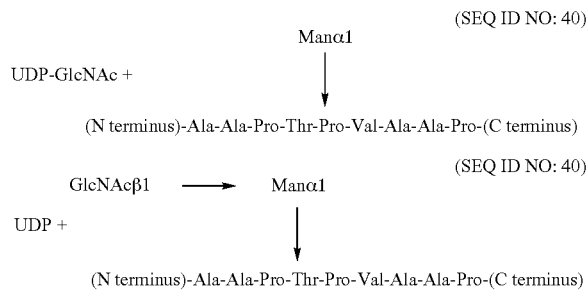

A yeast mutant which produces O-linked Man type sugar chain and glycoprotein of a mammalian cell can be prepared as described below.

First, a yeast mutant is prepared, in which an auxotrophic mutation trait for introducing exogenous polynucleotide is retained while yeast-specific genes for the biosynthesis of outer sugar chains are disrupted. In order to disrupt a target gene such as KRE2 (SEQ ID NO: 41), KTR1 (SEQ ID NO: 42, and KTR3 (SEQ ID NO: 43), a DNA fragment thereof is necessary, but the nucleotide sequence information of the DNA and its location on the chromosome have been revealed courtesy of the genome project on S. cerevisiae [Mewes. H. W., Albermann, K., Bahr, M., Frishman, D., Gleissner, A., Hani, J., Heumann, K., Kleine, K., Maierl, A., Oliver, S. G., Pfeiffer, F., and Zollner, A., Nature, (1997), 387 (suppl.), 7–8]. Therefore, the distribution of gene fragments including a vicinity of the target genes are available from public institutes such as ATCC (American Type Culture Collection) in the USA [ATCC Recombinant DNA materials, 3rd edition, 1993]. It is also possible to extract genomic DNA from S.cerevisiae by a general method and to obtain the target genes. The extraction of genomic DNA from S.cerevisiae can be carried out in accordance with, for example, a method by Cryer et al. [Cryer, D. R., Eccleshall, R., and Marmur, J., Methods Cell Biol., (1975), 12, 39–44] and a method by P. Philippsen et al. [Philippsen, P., Stotoz, A., and Scherf, C., Methods Enzymol., (1991), 194, 169–182]. Further, the target genes can be obtained by preparing primer DNAs based on the nucleotide sequence information and amplifying the targets by PCR with the genomic DNA of S. cerevisiae as a template.

In order to disrupt a plurality of target genes while retaining an auxotrophic mutation trait of the host yeast, a method is known wherein a hisG-URA3-hisG cassette having a DNA fragment of a hisG gene of Salmonella linked to both ends of a URA3 gene is employed [Alani, E., Cao, L., and Kleckner, N., Genetics, (1987), 116, 541–545]. First, the hisG-URA3-hisG cassette is inserted into a target gene in a plasmid using a restriction enzyme to construct a plasmid containing a disrupted allele. A Ura⁻ yeast is transformed with this plasmid and substitution with the target gene in the chromosome is carried out to obtain a gene-disrupted strain. The following methods can be adopted to transform yeast with the plasmid: a method wherein a plasmid is incorporated by treating with lithium salts to facilitate spontaneous DNA incorporation; and a method for electrically introducing DNA into a cell [Becker, D. M. and Guarente, L., Methods Enzymol., (1991), 194, 182–187]. The URA3 gene that has been inserted into the chromosome is sandwiched by hisGs and brings about homologous recombination between hisG sequences, so that the URA3 gene may be spontaneously dropped out of the chromosome together with one copy of hisG. In this case, one copy of a hisG fragment still remains in the disrupted target gene in the chromosome, and moreover the host cell becomes again an Ura⁻ phenotype. Ura3⁺ yeast strain is sensitive to 5-fluoroorotic acid (5-FOA) [Boeke, J. D., Trueheart, J., Natsoulis, G., and Fink, G. R., Methods Enzymol., (1987), 154, 165–174], and thus the cultivation using a medium added with 5-FOA enables the selective obtainment of the Ura⁻ yeast strain of interest. As a result of the above processes, a URA3 marker with auxotrophic mutation trait can be used again for the gene disruption of this yeast strain. For example, if KRE2, KTR1, and KTR3 are disrupted sequentially by repeatedly using this method, an auxotrophic triple disrupted strain (Δkre2Δktr1Δktr3) to which one mannose residue is linked as O-linked Man type sugar chain can be obtained.

If the polynucleotide encoding OMGnT of the present invention is introduced into this auxotrophic triple disrupted strain and expressed, O-linked Man type sugar chains of yeast can be changed to the GlcNAcα1→2Manα1→Ser/Thr observed in mammals. Although a yeast-specific O-linked Man type sugar chain has immunogenicity to mammals, such a problem is expected to be improved in the case of this sugar chain of yeast mutant (OMGnT, Δkre2Δktr1Δktr3). Further, when, without the use of auxotrophy as an index, a gene that imparts drug resistance is used as a marker and an OMGnT gene is introduced into yeast, any yeast mutant strain known as triple disrupted strains (Δkre2Δktr1Δktr3) [Lussier, M., Sdicu, A. M., Bussereau, F., Jacquet, M., and Bussey H., J. Biol. Chem. (1997) 272, 15527–15531] can be also used.

Furthermore, with this yeast mutant (OMGnT, Δkre2Δktr1Δktr3) used as a host, useful carbohydrates having mammalian O-linked Man type sugar chains (having GlcNAcβ1→2Man structure [Chiba, A., Matsumura, K., Yamada, H., Inazu, T., Shimizu, T., Kusunoki, S., Kanazawa, I., Kobata, A., and Endo, T., J. Biol. Chem., (1997), 272, 2156–2162; Sasaki, T., Yamada, H., Matsumura, K., Shimizu, T., Kobata, A., and Endo, T., Biochem. Biophys. Acta, (1998), 1425, 599–606; Smalheiser, N. R., Haslam, S. M., Sutton-Smith, M., Morris, H. R., and Dell, A., J. Biol. Chem., (1998), 273, 23698–23703; Yuen, C. T., Chai, W., Loveless, R. W., Lawson, A. M., Margolis, T., and Feizi, T., J. Biol. Chem., (1997), 272, 8924–8931]) can be produced en mass. To this end, the following methods are used: a method wherein a polynucleotide encoding a glycoprotein of interest is ligated to the downstream of a promoter capable of functioning in yeast and incorporated by homologous recombination into a host yeast cell; or a method wherein the polynucleotide is inserted into a suitable expression plasmid to transform the host. When the obtained yeast strain is cultivated by well-known methods, the yeast cells can produce the carbohydrates of interest intracellularly or extracellularly. The yeast cultivation can be carried out by conventional methods. For example, a synthetic medium (including carbon source, nitrogen source, inorganic salts, amino acids, and vitamins) may be used, to which various medium components supplied by Difco are added and from which amino acids that can be supplied with a marker necessary for duplication and retention of a plasmid, are removed [Sherman, F., Methods Enzymol., (1991), 194, 3–21]. In order to isolate and purify carbohydrates from the cultured product (culture solution, cultured cell bodies), any known method for isolation and purification may be suitably carried out. For example, after the completion of the cultivation, cells may be collected by centrifugation and suspended in an aqueous buffer solution. Then, the colleted cells may be disrupted by an ultrasonic grinder, French press, Menton Gaulin homogenizer, DYNO-Mill and the like to obtain a cell-free extract. From the supernatant obtained by centrifuging the cell-free extract, a purified preparation can be obtained using conventional methods for protein isolation and purification, alone or in combination of two or more, such as solvent extraction, salting-out, desalting, a precipitation method using an organic solvent, ion exchange chromatography, hydrophobic chromatography, gel filtration using a molecular sieve, affinity chromatography, chromatofocusing, and isoelectric focusing.

Further, as a method to liberate and prepare a sugar chain portion from a carbohydrate having O-linked Man type sugar chain linked thereto, β-elimination reaction with dilute alkali is known. For example, the glycoprotein obtained by the above purification, or the cells containing the glycoprotein are dissolved in 0.05N NaOH, 1M NaBH$_4$ and allowed to react at 45° C. for 18 hours, thereby enabling the sugar chain to be liberated. Furthermore, the resultant is adjusted to pH6.0 with 4N acetic acid, and then applied to an AG-50W-X12 (H+form) (Bio-Rad) column to collect a passing fraction and a fraction obtained by washing with water. The resultant is evaporated to dryness by an evaporator, and thereafter the operation of methanol dissolution and evaporation to dryness is repeated until boric acid is removed. The obtained sample may be applied to paper chromatography, Superdex Peptide HR10/30 (Amersham Pharmacia Biotech) column chromatography, or the like for isolation and purification [Chiba, A., Matsumura, K., Yamada, H., Inazu, T., Shimizu, T., Kusunoki, S., Kanazawa, I., Kobata, A., and Endo, T., J. Biol. Chem.(1997),272, 2156–2162, and Lussier, M., Camirand, A., Sdicu, A-M., and Bussey, H., Yeast.(1993),9,1057–1063].

EXAMPLES

Hereinafter, the present invention will be described with reference to Reference Examples and Examples, but the present invention is not limited to these examples.

(1) Reagents used in Refernce Examples and Examples

Unless specified otherwise, the reagents used herein were the highest grade products manufactured by Sigma Co. and Wako Pure Chemical Industries, Ltd. Further, the restriction enzymes used are those manufactured by Takara Shuzo Co., Ltd.

(2) Equipments used in Examples

Access RT-PCR System (Promega) was used for RT-PCR (Reverse transcription-polymerase chain reaction), and Advantage cDNA Polymerase Mix (Clontech) was used for amplifying DNA fragments of interest.

Further, ABI PLISM 377 DNA Sequencer (Perkin-Elmer) was used for gene sequence determination.

Reference Example 1

Preparation of Sugar Receptor Ac-Ala-Ala-Pro-Thr(Man)-Pro-Val-Ala-Ala-Pro-NH$_2$ (Man-peptide) (SEQ ID NO: 40)

Fmoc-Thr(Man)-OH was synthesized as follows. In the presence of N-iodosuccinimide and trifluoromethanesulfonic acid, phenyl 2,3,4,6,-tetra-O-benzyl-1-thio-D-mannopyranoside and N-benzyloxycarbonyl-L-threonine benzyl ester (Z-Thr-OBzl) were reacted, and Z-Thr (Man(OBzl)$_4$-OBzl protected with a benzyl group was obtained with a yield of 77%. After deprotection of all benzyl groups and Z groups by hydrogenation with catalysts, Fmoc-OSu was reacted with the resultants, thereby obtaining Fmoc-Thr (Man)-OH with a yield of 75%.

Ac-Ala-Ala-Pro-Thr(Man)-Pro-Val-Ala-Ala-Pro-NH$_2$ (SEQ ID NO: 40) was synthesized by Fmoc solid phase method [Mizuo, M., Muramoto, I., Kawakami, T., Seike, M., Aimoto, S., Haneda, K., and Inazu, T., Tetrahedron Lett., (1998), 39, 55–58]. Crude product was obtained from sugar peptide resins by deprotection, and the purified Man-peptides of interest were obtained by purification with column chromatography using a C18 reverse phase column (Inertsil ODS-3, 20×250 mm) manufactured by GL Sciences Inc. The separation was carried out by concentration gradient using 0.1% TFA (Solution A) and acetonitrile containing 0.1% TFA (Solution B) at 45° C. and 10 ml/min flow rate, and the detection was carried out at 214 nm. For concentration gradient, after running 5% Solution B until 25 min., the concentration of Solution B was linearly increased to 35% until 35 min. The structure of the obtained Man-peptide was confirmed by $^1$H-NMR, amino acid composition analysis, and MALDI-TOF MS (matrix-assisted laser desorption inonization time of flight mass spectrometry).

Example 1

Specific Assay Method for OMGnT Activity

There has never been any report on an assay method for OMGnT activity. Therefore, the present inventors developed a novel assay method for OMGnT activity and used it for the following examples.

The enzyme solution was added to 140 mM MES [2-(N-morpholino) ethanesulfonic acid] buffer (pH 7.0) containing 0.4 mM Man-peptide, 0.2 mM UDP-[$^3$H]GlcNAc (up to 228,000 dpm/nmol), 10 mM MnCl$_2$, 5 mM AMP, 200 mM GlcNAc, 2%(w/v) Triton X-100, 10% glycerol, 2 µg/ml antipain, 2 µg/ml chymostatin, 3 µg/ml pepstatin A, 2 µg/ml leupeptin, 1 mM benzamidine-HCl, and 1 mM PMSF (phenylmethylsulfonyl fluoride) to prepare 50 µl of reaction solution. After the reaction at 37° C. for 3 hours, the reaction was terminated by 3 minutes of boiling. The reaction mixture was then filtered with a filter Ultrafree-MC (Millipore) having a pore size of 0.22 µm to remove solids, and analyzed by Wakopak 5C18-200 column (4.6×250 mm, Wako Pure Chemical Industries, Ltd.). The separation was carried out using concentration gradient with Solution A and Solution B at a flow rate of 1.0 ml/min. For concentration gradient, the concentration of Solution B was 0% until 10 min and linearly increased to 25% until 35 min, and further linearly increased to 100% over a period of 40 min. Peptide detection was carried out at 214 nm, and the radioactivity of each fraction was assayed using a liquid scintillation counter.

Figure 1:
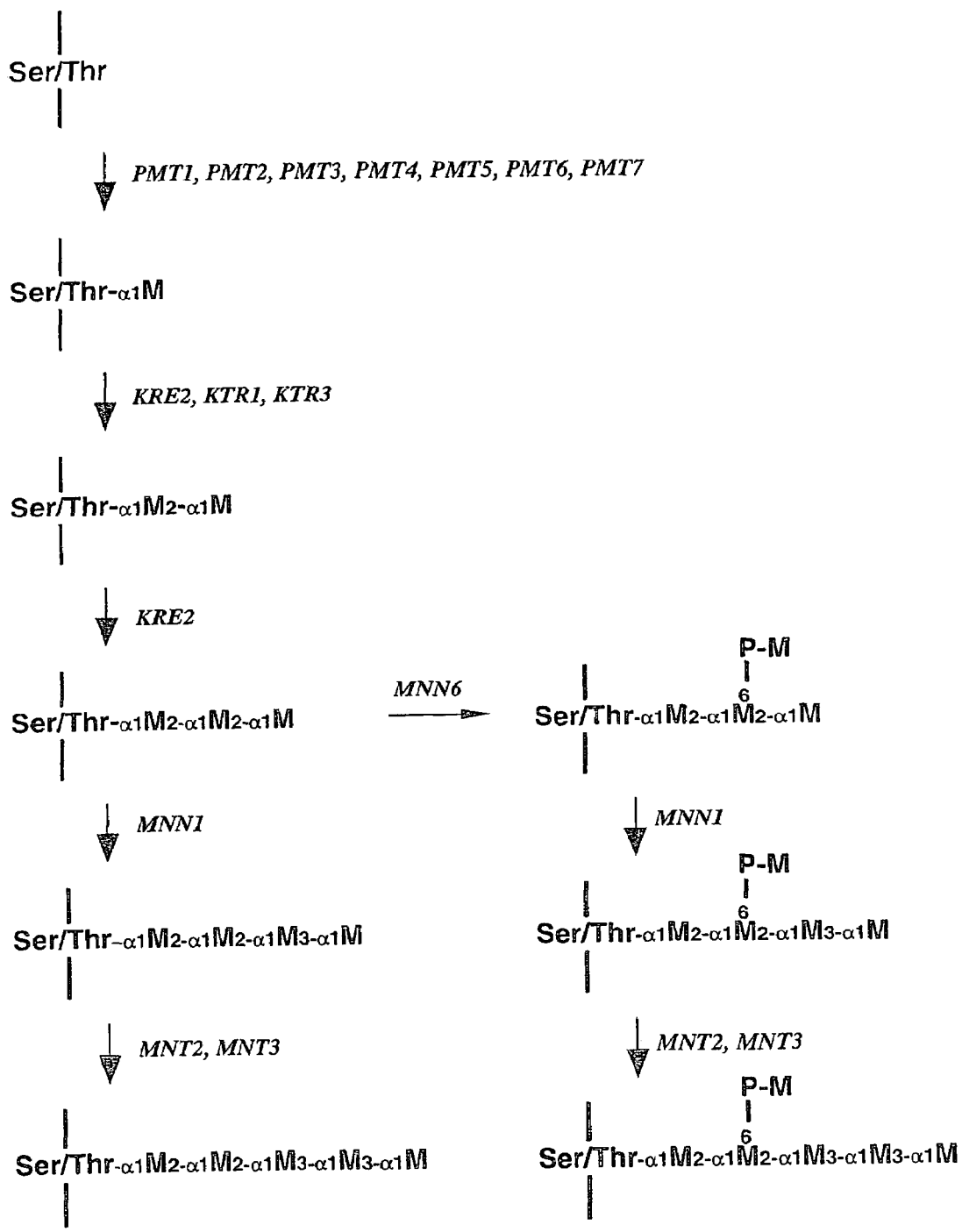
FIG. 1 shows a biosynthesis pathway of an O-linked Man type sugar chain in *Saccharomyces cerevisiae*.
Figure 2:
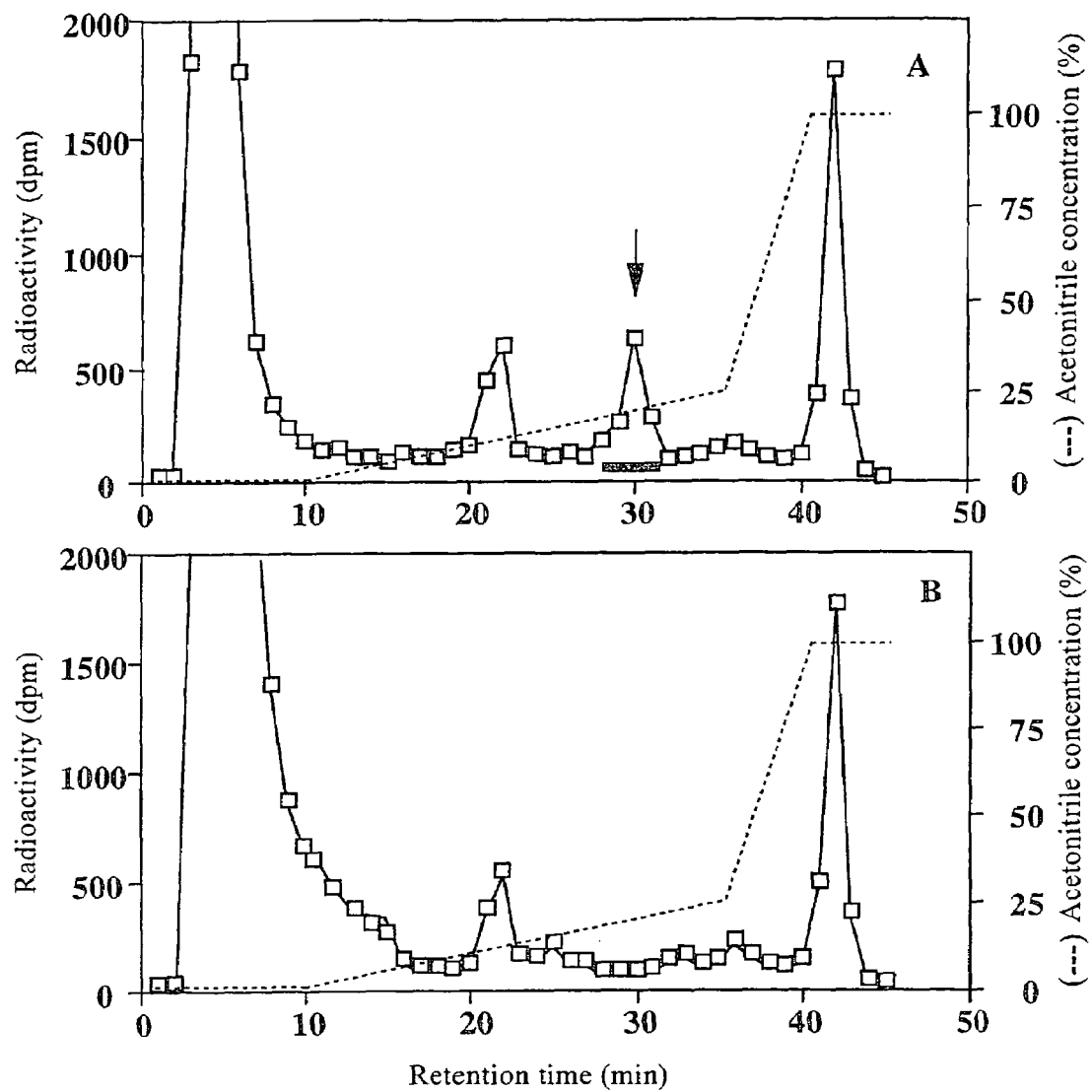
FIG. 2 shows an OMGnT activity assay by reverse phase HPLC.

FIG. 2 shows a typical result. A peak appearing at around 30 minute corresponds to the product Man-peptide to which [$^3$H]GlcNAc was transferred, and the activity can be calculated by its radioactivity.

The O-linked type sugar chain structure of the product was examined by the method described as follows. The product was dissolved in 500 µl of 0.05N NaOH and 1M NaBH$_4$ and brought into reaction at 45° C. for 18 hours to liberate sugar chains from peptides. The mixture was adjusted to pH 5.0 with 4N acetic acid, and thereafter applied to 1 ml AG-50W-X8 (H+form) (Bio-Rad) column to collect in bulk a passing fraction and washing fraction with 10 ml of water. The collected mixture was evaporated to dryness, and the operation of dissolution with methanol and evaporation to dryness was repeated until boric acid was removed. The obtained sample was applied to Superdex Peptide HR10/30 (Amersham Pharmacia Biotech) column chromatography at 60° C. and a radioactive fraction was collected. The obtained sugar chain was analyzed by HPAEC-PAD (High-pH anion-exchange chromatography with pulsed amperometric detection) using a CarboPac PA-1 column (Dionex) [Kotani, N. and Takasaki, S., Anal. Biochem., (1998), 264, 66–73]. The separation was carried out at a flow rate of 1.0 ml/min. with 15 mM NaOH.

As shown in FIG. 3, the obtained sugar chain had a completely identical elution position to that of GlcNAcβ1→2Man$_{OH}$, and it was confirmed that OMGnT transferred GlcNac via β 1→2 linkage to Man-peptide.

Incidentally, GlcNAcβ1→2Man$_{OH}$ was prepared by reducing GlcNAcβ1→2Man (Dextra Laboratory) with NaBH$_4$ [Chiba, A., Matsumura, K., Yamada, H., Inazu, T., Shimizu, T., Kusunoki, S., Kanazawa, I., Kobata, A., and Endo, T., J. Biol. Chem., (1997), 272, 2156–2162].

Reference Example 2

Assay Method for GnT-I Activity

The activity of GnT-1 was assayed with a method by Yoshida et al. [Yoshida, S., Suzuki, M., Yamano, S., Takeuchi, M., Ikenaga, H., Kioka, N., Sakai, H., and Komano, T., Glycobiology, (1999), 9, 53–58] as described below. A 20 µl reaction solution was prepared by adding an enzyme source thereto so as to have a final concentration of 100 mM MES (pH 6.0), 20 mM MnCl$_2$, 5 µM Manα1–6(Manα1–3)Manα1–6(Manα1–3)Manβ1–4GlcNAcβ1–4GlcNAc-PA (M5GN2-PA; Takara Shuzo, PA-Sugar Chain 017), 1 mM UDP-GlcNAc, 100 mM GlcNAc, 5 mM AMP, 1% Triton X-100, and 0.2% BSA. The reaction solution was incubated at 37° C. for 1 hour, and the reaction was terminated in boiling water. Thereafter, the reaction solution was analyzed by a reverse phase HPLC (Cosmosil 5C18-AR column) available from Nacalai Tesque.

When Manα1–6(Manα1–3)Manβ1–4GlcNAcβ1–4GlcNAc-PA (M3GN2-PA; Takara Shuzo, PA-Sugar Chain 016) was used as a sugar receptor, the same method was employed for analysis.

Example 2

Preparation of Enzyme Having OMGnT Activity and Requirement of Divalent Cation by the Enzyme (1) Preparation of Crude Enzyme To 1 g of animal tissue or cultured cells, 9 ml of 10 mM Tris-HCl (pH7.4) containing 2 µg/ml antipain, 2 µg/ml chymostatin, 3 µg/ml pepstatin A, 2 µg/ml leupeptin, 1 mM benzamidine-HCl, and 1 mM PMSF, 1 mM EDTA, and 250 mM Sucrose were added, and the mixture was homogenized by a Potter homogenizer (digital homogenizer: Iuchi). The mixture was centrifuged for 10 minutes at 900×g, and then the obtained supernatant was centrifuged for 1 hour at 100,000×g, thereby obtaining a microsomal fraction as a precipitate. In the case of preparing solubilized enzyme, the precipitate was suspended in 140 mM MES buffer (pH 7.0) (referred to as solubilization buffer) containing 5 mM AMP, 200 mM GlcNAc, 2%(w/v) Triton X-100, 10% glycerol, 2 µg/ml antipain, 2 µg/ml chymostatin, 3 µg/ml pepstatin A, 2 µg/ml leupeptin, 1 mM benzamidine-HCl, and 1 mM PMSF (phenylmethylsulfonyl fluoride) and sonicated. Thereafter, the resultant was centrifuged for 1 hour at 100,000×g and the obtained supernatant was used.

OMGnT exists widely in animal organs and cells. In the case of, for example, mammals, enzyme solutions prepared from a newborn rat brain, a rat brain, a swine brain, a bovine brain, a rat schwannoma cell RT-4, and a mouse myoblast cell C2C12 were examined by the method described in Example 1, and all of them exhibited OMGnT activity (Table 1). The amount of protein was assayed using BCA protein assay (Pierce) with BSA (bovine serum albumin) as a standard substance.

TABLE 1

| Enzyme source | Activity (pmol/hr/mg protein) |
| --- | --- |
| Newborn rat brain | 66.7 |
| Rat brain | 91.2 |
| Swine brain | 25.5 |
| Bovine brain | 1.8 |

TABLE 1-continued

| Enzyme source | Activity (pmol/hr/mg protein) |
|---|---|
| Rat schwannoma cell RT-4 | 46.8 |
| Mouse myoblast cell C2C12 | 24.4 |

(2) Requirement of Divalent Cation

Table 2 shows the result of the examination on divalent cation requirement for enzyme activity using OMGnT derived from a newborn rat brain. This enzyme was deactivated by the addition of EDTA (ethylene diamine tetraacetic acid), and a divalent cation ($Mn^{2+}$, $Mg^{2+}$, $Ca^{2+}$) was essential for its activity expression. Among them, $Mn^{2+}$ showed the greatest effect, followed by $Mg^{2+}$, and weak effect was recognized in $Ca^{2+}$.

TABLE 2

| Additive | Relative activity of OMGnT (%) |
|---|---|
| None | 6 |
| EDTA | 0 |
| $MnCl_2$ | 100 |
| $MgCl_2$ | 39 |
| $CaCl_2$ | 15 |

*OMGnT activity was determined by adding each of the metal ions (10 mM) to a OMGnT sample. The figures in the Table are expressed in percent, taking the activity when 10 mM $MnCl_2$ is added as 100%.

Example 3

Isolation and Nucleotide Sequence Analysis of a Partial cDNA of Human OMGnT (1) Search of cDNA Homologous to Human GnT-I An EST (expressed sequence tag) clone containing cDNA highly homologous to human GnT-I was searched for in the Gene Bank by BLAST. As a result, AA911248, F11377, W77826, R20086, AA422183 were found. Further, an EST clone containing cDNA overlapping with these cDNAs was searched for, and as a result, AA843652 or the like was found.

In order to confirm these cDNA sequences, gene amplification was performed by RT-PCR using the Total RNA derived from a human liver, lung, small intestine, and brain, hGnTn1 F1 primer: GACCAGTCCTGCTGAAGACAGAT (SEQ ID NO: 3) and hGnTn1 R1 primer: GGTCCAGGTG-GTGAAGTCATCAT (SEQ ID NO: 4). For the RT-PCR, Access RT-PCR kit (Promega) was used, and the Total RNA derived from a human liver, lung, small intestine, and brain was purchased from Clontech. As a result, a DNA fragment of approximately 1.1 kb was amplified for all the RNAs. The RT-PCR product from human brain RNA was subcloned into pCR-TOPO 2.1 (Invitrogen) using a TOPO TA cloning kit (Invitrogen), followed by analysis of the nucleotide sequence thereof. After the sequence reaction using Thermo Sequenase II Dye Terminator Cycle Sequencing Kit (Amersham Pharmacia Biotech), the determination of the nucleotide sequence was conducted by analysis with a 377DNA sequencer manufactured by Perkin Elmer. As a result, the cDNA sequence of 1069 bp was revealed and this cDNA sequence was found to have 7 different sites from the sequence having EST clones ligated each other. Further, it was suggested that this sequence encodes an amino acid sequence having high homology to human GnT-I.

(2) Obtainment of Human OMGnT cDNA

However, in the sequence obtained in (1) above, a stop codon was not found. Therefore, to obtain a downstream region, an RT-PCR was performed using total RNA derived from human brain, hGnTn1 F3 primer:CCAGCTCAG-GAATGTGGACAGTC (SEQ ID NO: 5) and hGnTn1 R2 primer:TTCAAGGCCCTCAGGACAGTC (SEQ ID NO: 6). As a result, a DNA fragment of approximately 0.7 kb was amplified and the amplified fragment was subcloned into pCR-TOPO 2.1, followed by analysis of the nucleotide sequence thereof. The cDNA sequence of 693 bp was revealed, which had 4 different sites from the reported sequence of an EST clone. It was recognized that this sequence had a stop codon in a frame having high sequence homology to human GnT-I, and it was thought that a gene at C-terminal side was completely obtained.

On the other hand, a transmembrane domain, which is recognized in many glycosyltransferases, was not recognized in the above cDNA region, and thus it was presumed that the N-terminal side of the structural gene was not included. Hence, using human brain-derived Marathon-Ready cDNA (Clontech), a 5'-RACE (Rapid amplification of cDNA ends) was performed. The PCR was performed in two stages. For the first stage, hGnTn1 R1 primer:GGTCCAG-GTGGTGAAGTCATCAT (SEQ ID NO: 4) and AP1 primer (Clontech): CCATCCTAATACGACTCACTATAGGGC (SEQ ID NO: 7) were used in combination. For the second stage, hGnTn1 R5 primer: GCTGAGCTCAATGGCA-CATCTG (SEQ ID NO: 8) and AP2 primer (Clontech): ACTCACTATAGGGCTCGAGCGGC (SEQ ID NO: 9) were used in combination. The PCR product was subcloned into pCR-TOPO 2.1, followed by analysis of the nucleotide sequence thereof. A cDNA sequence of 827 bp was revealed. In this cDNA sequence, a stop codon was recognized in an upstream portion of a frame having high sequence homology to human GnT-I, and therefore ATG (95–97) was presumed to be the initiation methionine.

From the results of the above RT-PCR and 5'-RACE, the nucleotide sequence of human OMGnT cDNA as shown in SEQ ID NO: 1 and the amino acid sequence of human OMGnT as shown in SEQ ID NO: 2 have been revealed. The human OMGnT is a protein consisting of 660 amino acids, and according to secondary structure prediction and hydropathy analysis, it is considered to be a type II membrane protein wherein 17 amino acids from 43: Ala to 59: Leu were presumed to be a transmembrane region.

The preparation of cDNA encoding human OMGnT is described in Example 5.

Example 4

Expression Vector Preparation, Expression, Activity Assay, and Properties of Solubilized Human OMGnT Enzyme (1) Preparation of Secretory Expression Vector pcDNA3.1 IHXneo for Solubilized Glycosyltransferase In order to express solubilized human OMGnT enzyme, a secretory expression vector was constructed as follows. Using pSecTag2 (Invitrogen) as a template, and pcDNA F primer: TTGACGCAAATGGGCGGTAGGC (SEQ ID NO: 10) and Ig-His R primer: GAGAACCCCCGGCCG-GCTGGGCCGCGTCAC (SEQ ID NO: 11) as primers, a DNA of Ig kappa chain secretory signal was amplified by PCR. Also, using pcDNA3.1 H is C (Invitrogen) as a template, and Ig-His F primer: CCAGCCGGCCGGGGGT-TCTCATCATCATCAT (SEQ ID NO: 12), and pcDNA R primer: TAGAAGGCACAGTCGAGGCTG (SEQ ID NO: 13) as primers, a gene consecutively having His-tag, Xpress epitope, and multi-cloning site was amplified by PCR. Further, using a mixture of the above obtained PCR products as a template, and pcDNA F primer:TTGACGCAAATGGGCGGTAGGC (SEQ ID NO: 10), and pcDNA R primer:TAGAAGGCACAGTCGAGGCTG (SEQ ID NO: 13) as primers, a DNA having Ig kappa chain secretory signal, Hig-tag, Xpress epitope, and multi-cloning site ligated was amplified by PCR. The obtained DNA fragment of approximately 0.4 kb was digested with Sac I and Apa I, and inserted into a similar site of pcDNA3.1 H is C, thereby preparing a secretory expression vector pcDNA3.1 IHXneo.

(2) Preparation of Secretory Expression Vectors sOMGnT (S)/pcDNA3.1 IHXneo and sOMGnT(L)/pcDNA3.1 IHXzeo for Solubilized Human OMGnT Enzyme Two types of solubilized enzymes of human OMGnT: His-Xpress-sOMGnT(S) and His-Xpress-sOMGnT(L), were expressed and secreted in a HEK293T cell. His-Xpress-sOMGnT (S) and His-Xpress-sOMGnT (L) are proteins comprising 414 amino acids from 247: Ser of human OMGnT ((247: Ser to 660: Thr) SEQ ID NO: 2), and 595 amino acids from 66: Ser thereof (66: Ser to 660: Thr), respectively. In addition, as a control, solubilized human GnT-I enzyme His-Xpress-sGnT-I was also expressed. This is a protein comprising 407 amino acids from 39: Ser of the amino acid sequence of GnT-I as described in Kumar, R., Yang, J., Larsen, R. D. and Stanley P., Proc. Natl. Acad. Sci. USA, (1990), 87, 9948–9952.

cDNA of human solubilized OMGnT (S) was amplified by RT-PCR using RNA derived from human brain, hGnTn1 F4 primer: AAGGATCCTCAGCAGAAGAGGCA-GAGTGC (SEQ ID No: 14), and hGnTn1 R4 primer: TTCTCGAGGGTCCTGGAGGAGGTCTCAT (SEQ ID NO: 15). The obtained DNA fragment of approximately 1.3 kb was digested with BamHI and XhoI and inserted into a similar site of pcDNA3.1 IHXneo, thereby preparing an expression plasmid sOMGnT(S)/pcDNA3.1 IHXneo.

The expression plasmid sOMGnT(L)/pcDNA3.1 IHXzeo for human solubilized OMGnT (L) was prepared as follows. First, sOMGnT(S)/pcDNA3.1 IHXneo was digested with SacI and ApaI to obtain a fragment of approximately 1.5 kb encoding Ig-His-Xpress epitope-sOMGnT. This DNA fragment was inserted into a similar site of pcDNA3.1 Zeo(+) (Invitrogen) to construct sOMGnT(S)/pcDNA3.1 IHXzeo. Next, using RNA derived from human brain, hGnTn1 F6 primer:GCGGATCCAGTGAAGCCAATGAAGACCCAG (SEQ ID NO: 16), and hGnTn1 R6 primer:GCAGCTG-CATACACTTCCATAGC (SEQ ID NO: 17), cDNA was amplified by RT-PCR. The obtained DNA fragment of approximately 1.0 kb was digested with BamHI and PstI and inserted into a similar site of sOMGnT(S)/pcDNA3.1 IHXzeo to prepare an expression plasmid sOMGnT(L)/pcDNA3.1 IHXzeo.

(3) Preparation of Secretory Expression Vector sGnT-I/pcDNA3.1 IHXneo for Solubilized Human GnT-I enzyme cDNA of solubilized human GnT-I was amplified by RT-PCR using RNA derived from human brain, hGnTI F1 primer: CAGGATCCGTCAGCGCTCTCGATGGCGACC (SEQ ID NO: 18), and hGnTI R1 primer: CTCCTCGAG-GAAGGACAGGCAGGTGCTAA (SEQ ID NO: 19). The obtained DNA fragment of approximately 1.3 kb was digested with BamHI and XhoI and inserted into a similar site of pcDNA3.1 IHXneo to prepare an expression plasmid sGnT-I/pcDNA3.1 IHXneo.

(4) Expression of Various Secretory Expression Vectors

Each secretory expression plasmid was transiently expressed in a HEK293T cell derived from human embryonic kidney. Usually, HEK293T cells were cultured in D-MEM (Gibco, #11995-065) containing 10% Fetal Calf Serum (Hyclone), 10 mM MEM Non-Essential Amino Acids solution (Gibco), 2 mM Glutamine (Gibco), and 100 units/ml Penicillin/100 µg/ml Streptomycin (Gibco). In a 6-well plate, 2 µg of plasmid was transfected into 50 to 70% confluent cells by calcium phosphate method. After overnight cultivation, the medium exchange was performed and the cultivation was continued for 48 hours [Pear, W. S., Nolan, G. P., Scott, M. L. and Baltimore, D., Proc. Natl. Acad. Sci. USA, (1993), 90, 8392–8396]. Further, the medium was exchanged with a serum-free medium, and after 48-hour cultivation, the supernatant was collected.

(5) Western Blotting Analysis of Solubilized Human OMGnT and GnT-I Enzymes

100 µl of the serum-free medium containing transfectants was concentrated to 10 µl with microcon-30 and the resultant was applied to SDS-PAGE with 15–25% gradient gel. The SDS-PAGE was performed based on a method by Laemmli [Laemmli, U. K. Nature (1970) 313, 756–762]. After electrophoresis was performed, the protein was transferred to a PVDF membrane (Immobilon-P) manufactured by Millipore. The membrane was subjected to blocking with 10% skim milk, and then allowed to react with primary antibodies 1/5000 Anti-Xpress Antibody (Invitrogen) and secondary antibodies 1/5000 Horseradish Peroxidase linked Anti-mouse Ig whole Antibody (Amersham Pharmacia Biotech). The detection was performed with ECL western blotting detection reagents (Amersham Pharmacia Biotech).

From the results shown in FIG. 4, it was confirmed that His-Xpress-sOMGnT(S), His-Xpress-sOMGnT(L), and His-Xpress-sGnT-I were all expressed at almost equivalent levels. Additionally, individual molecular weights were calculated as approximately 52, 76 and 52 KDa, based on the mobility on SDS-PAGE.

(6) Enzyme activity of solubilized enzymes human OMGnT and GnT-I

According to the method described in Example 1, OMGnT activity in the serum-free medium was assayed. As shown in Table 3, almost no activity was detected in His-Xpress-sGnT-1, but in contrast, significantly high OMGnT activity was recognized in His-Xpress-sOMGnT (S) and His-Xpress-sOMGnT(L). This result confirmed that OMGnT cDNA, as shown in SEQ ID NO: 1, encodes glycosyltransferase OMGnT and the region responsible for enzyme activity exists in 414 amino acids from 247: Ser (247: Ser to 660: Thr). Further, it was indicated that solubilized enzyme of OMGnT, which is inherently a membrane-bound protein, can be produced in a supernatant of cell culture.

In contrast, when GnT-I activity was assayed by the method described in Reference Example 2, His-Xpress-sGnT-I exhibited high level of activity at 500 pmol/hr/ml medium. However, both His-Xpress-sOMGnT(S) and His-Xpress-sOMGnT(L) did not exhibit activity at all. From these results, OMGnT is considered to have no GnT-I activity.

TABLE 3

| Plasmid | OMGnT activity (pmol/hr/mg protein) |
| --- | --- |
| sOMGnT(S)/pcDNA3.1 IHXneo | 20 |
| sOMGnT(L)/pcDNA3.1 IHXzeo | 15 |
| sGnT-I/pcDNA3.1 IHXneo | 0.4 |

(7) Substrate Specificity and Kinetic Parameters of Solubilized Human OMGnT Enzyme (7-1) Substrate Specificity Table 4 shows the results of the examination on substrate specificity regarding sugar receptors using solubilized human OMGnT enzymes (His-Xpress-sOMGnT (S) and His-Xpress-sOMGnT(L)). These two types of solubilized enzymes both use Man-peptide as a receptor, but do not use Man, p-nitrophenyl Man, M5GN2-PA, and M3GN2-PA as receptors. They exhibited a reactivity of 0% toward Man, p-nitrophenyl Man, M5GN2-PA, and M3GN2-PA, wherein the activity when Man-peptide was used as a receptor is regarded as 100%.

TABLE 4

| | OMGnT relative activity (%) | |
| --- | --- | --- |
| Sugar receptor | His-Xpress-sOMGnT(S) | His-Xpress-sOMGnT(L) |
| Man-peptide | 100 | 100 |
| Man | 0 | 0 |
| p-nitrophenyl Man | 0 | 0 |
| M5GN2-PA | 0 | 0 |
| M3GN2-PA | 0 | 0 |

(7-2) Kinetic Parameters

Km value of His-Xpress-sOMGnT (L) toward Man-peptide obtained by the assay method of Example 2 was 1.85 mM, and, apparent Km value toward UDP-GlcNAc was 0.73 mM, respectively. In addition, Km value of His-Xpress-sOMGnT (S) toward Man-peptide was 1.36 mM, and apparent Km value toward UDP-GlcNAc was 0.57 mM, respectively.

Example 5

Preparation of Human Full-Length OMGnT Expression Plasmid, Preparation of OMGnT Activity-Enforced Cells, and OMGnT Activity Assay in the Cells (1) Preparation of Human OMGnT Expression Plasmid OMGnT/pcDNA3.1 Zeo cDNA encoding the N-terminal region of human OMGnT was amplified by RT-PCR using RNA derived from human brain, hGnTn1 F5 primer: TTTGCTAGCCAATCCGG-TATGGACGACTGG (SEQ ID NO: 20), and hGnTn1 R6 primer: GCAGCTGCATACACTTCCATAGC (SEQ ID NO: 17). The obtained DNA fragment of approximately 0.9 kb was digested with NheI and PstI and inserted into a similar site of sOMGnT(S)/pcDNA3.1 IHXzeo to prepare an expression plasmid OMGnT/pcDNA3.1 zeo. This plasmid can be considered to be a plasmid in which a cDNA of approximately 2.0 kb encoding the full length of human OMGnT is inserted into a site between NheI and XhoI of pcDNA3.1 Zeo(+).

(2) Expression and Activity Assay of Human OMGnT

The expression plasmid was transiently expressed in an HEK293T cell in the same manner as described in Example 3. 15 µg of plasmid was transfected to 50–70% confluent cells in a 10 cm petri dish. After overnight cultivation, the medium was changed. After a further 48-hour cultivation, cells were collected.

A microsomal fraction was prepared from cells by the method described in Example 2, and OMGnT activity of a soluble fraction and an insoluble fraction were assayed by the method described in Example 1. The results are shown in FIG. 5.

In both the soluble fraction and insoluble fraction of OMGnT cDNA transfectants, high activity of about 120 and 140 times higher than those of the control (no plasmid) which were not transfected with the plasmid, was detected, respectively. From this result, OMGnT cDNA as shown in SEQ ID NO: 1 was confirmed to encode a glycosyltransferase, OMGnT. Further, even when the microsomal fraction prepared from the OMGnT cDNA transfectants was sonicated in the presence of surfactants, high activity was still recognized in the insoluble fraction, indicating that OMGnT was a membrane protein as expected from the amino acid sequence. Additionally, weak OMGnT activity was detected in soluble fraction and the insoluble fraction of the control (no plasmid). This proves OMGnT exists widely in animal cells and they can be enzyme sources as mentioned in Example 2.

As described above, the introduction of OMGnT cDNA into a cell enables the production of OMGnT activity-reinforced cells.

TABLE 5

| | OMGnT activity (pmol/hr/mg protein) | | |
| --- | --- | --- | --- |
| Plasmid | Soluble fraction | Insoluble fraction | Total |
| None | 1.5 | 1.7 | 3.2 |
| OMGnT/pcDNA3.1zeo | 182.7 | 243.9 | 426.6 |

Example 6

Expression and Activity Assay of OMGnT in Budding Yeast (1) Construction of OMGnT Expression Vector In order to confirm the expression of OMGnT protein, a vector was constructed, which expresses OMGnT having an epitope sequence of vesicular stomatitis virus glycoprotein (VSV-G) (Kreis, EMBO J., 5, 931–941 (1986)) as a tag added to the N-terminus thereof. Namely, a region having enzyme activity of OMGnT was first excised from OMGnT/pcDNA3.1 zeo prepared in Example 5 with KpnI and XhoI, and inserted into a site between KpnI and XhoI sites of the yeast expression vector YEp352GAP (Kainuma et al., Glycobiology, 9, 133–141 (1999)). The resultant plasmid was designated as YEp352-OMGnT1. Next, using YF1 primer (TGAATAGATTGGGTAAGATGGACGACTG-GAAGCCC: SEQ ID NO: 21) and YR1 primer (CCCAGTGGCACTCTGCCTCTTCTGC: SEQ ID NO: 22), a chimeric gene encoding a partial protein of OMGnT having VSV-G epitope added to the N-terminus thereof was amplified with the use of OMGnT/pcDNA3.1 zeo as a template. Further, using this DNA fragment as a template, and YF2 primer (CCCGAATTCATGTACACTGATAT-TGAAATGAATAGATTGGGTAAG: SEQ ID No: 23) and the above YR1 primer, the amplification was performed by PCR, and EcoRI site was introduced. After confirming the sequence of the amplified DNA fragment, it was treated with restriction enzymes EcoRI and SacI and inserted into a site between EcoRI and SacI sites of YEp352-OMGnT1, thereby attaining an expression vector YEp-OMGnT of interest.

Also, to enhance the expression level in yeast and effectively localize the protein in the Golgi apparatus, a chimeric gene was prepared, which encodes a portion of a transmembrane region of a gene (OCH1) (Nakayama, et al., EMBO J., 11, 2511–2519 (1992)) encoding α-1,6-mannosyltransferase of yeast, and a region for enzyme activity of OMGnT. First, using YF3 primer (TGAATAGATTGGGTAAGAT-GTCTAGGAAGTTGTCCC: SEQ ID NO: 24) and YR2 primer (GGGGAGCTCAAATTTATATCTTGTG: SEQ ID No:25) with the genomic DNA of W303-1A as a template, a chimeric gene was amplified, which encoded a protein (VSV-G-Och1pTM-OMGnT) having a VSV-G epitope added to a transmembrane region of OCH1 protein (Met1 to Leu64). Next, using this DNA fragment as a template, and the above YF2 primer and YR1 primer, amplification was performed by PCR, and EcoRI site was introduced thereinto. After confirming the sequence of the amplified DNA fragment, it was treated with restriction enzymes EcoRI and SacI, and inserted into a site between EcoRI and SacI of YEp352-OMGnT1. This plasmid was designated as YEp-OCH1-OMGnT.

Using the two types of plasmids, YEp-OMGnT and YEp-OCH1-OMGnT, budding yeasts (*S cerevisiae* W303-1A) as host cells were transformed by the lithium acetate method. After the transformation, they were plated onto an SD-Ura medium plate and cultured at 30° C. for 2 days, thereby obtaining individual transformants. A strain having YEp-OMGnT and a strain having YEp-OCH1—OMGnT were designated as SSY1 and SSY2, respectively.

(2) Expression confirmation and activity assay of OMGnT in budding yeasts

The confirmation of OMGnT expression in budding yeast was carried out using the Western blotting method.

First, the obtained transformants were subjected to liquid culture with 500 ml of SD-Ura solution, and then harvested. After washing with cold water, the cells were suspended in 5.7 ml of Spheroplast medium (50 mM potassium phosphate (pH 7.5) containing 1 M sorbitol). 9 μl of 2-mercaptoethanol and 12 mg of Zymolyase 100T were dissolved in 300 μl of Spheroplast medium and the mixture was added to the suspension. The resultant mixture was incubated at 30° C. for 45 minutes. Further, 15 ml of 1 M sorbitol was added thereto and the mixture was centrifuged. Thereafter, the precipitate was washed with 15 ml of 1 M sorbitol again and harvested. To this precipitate, 4 ml of lysis buffer (10 mM triethanolamine (pH 7.2) solution containing 250 mM sorbitol, 2 μg/ml antipain, 2 μg/ml chymostatin, 3 μg/ml leupeptin, 3 μg/ml pepstatin, 1 mM benzamidine, 1 mM EDTA, 1 mM EGTA, and 1 mM PMSF) was added. Cells were destroyed with a homogenizer and centrifuged at 220 ×g to recover a supernatant. This supernatant was further centrifuged at 10,000 ×g and the precipitated fraction was suspended in 150 μl of lysis buffer, which was regarded as P2 fraction. The supernatant was further centrifuged at 100,000×g and the precipitated fraction was suspended in 150 μl of lysis buffer, which was regarded as P3 fraction.

P2 and P3 fractions each containing a protein mass of 50 μg was separated respectively by SDS-PAGE, and then the resultant was transferred to a PVDF membrane and used for Western blotting analysis in accordance with conventional methods. A mouse anti-VSV-G antibody (Clontech) was used as a primary antibody and a rabbit anti-mouse Ig antibody-alkaline phosphatase complex (ICN Pharmaceuticals) was used as a secondary antibody. The detection was performed by exposing the target on X-ray film using Super Signal Ultra (Pierce) as a substrate. The results are shown in FIG. 5. In comparison with the strain having only the vector, several signals were observed for W303-1A/YEp-OMGnT and one signal was observed for W303-1A/YEp-OCH1-OMGnT, but W303-1A/YEp-OMGnT exhibited stronger signal. In addition, a strong signal was observed in both strains from the P2 fraction containing intracellular endoplasmic recticula or the like.

Next, OMGnT activity of the P2 and P3 fractions of each strain was assayed. The activity assay was performed by the method described in Example 1. The results are shown in Table 6. The control having only the vector exhibited no activity, while SSY1 and SSY2 both exhibited clear OMGnT activity. Further, P2 fraction exhibited higher activity than P3 fraction for both strains.

TABLE 6

| Enzyme source | Activity (pmol/hr/mg crude protein) |
| --- | --- |
| W303-1A/YEp352 P2 | 0 |
| W303-1A/YEp352 P3 | 0 |
| SSY1 P2 | 193 |
| SSY1 P3 | 87 |
| SSY2 P2 | 229 |
| SSY2 P3 | 141 |

From these results, it was confirmed that active OMGnT protein could be expressed in yeast. Additionally, combining the results of Western blotting and activity assay together, SSY2, which had a lower expression level of OMGnT was considered to have a higher OMGnT specific activity. Thus, a chimeric gene with OCH1 was used for Examples described below.

Example 7

Breeding of Yeast Mutant (Triple Disrupted Strain Retaining Δ kre2 Δ ktr1 Δ ktr3 Marker) with the Lack of Yeast Specific O-Linked Man Type Sugar Chain (1) Preparation of Disrupted Strain Retaining Δ kre2 Marker and its Properties A cassette (HUH) in which Salmonella hisG gene was linked to both ends of URA3 gene by direct repeat was cleaved at BglII and BamHI from pNK51 that has been already reported (Alani et al., Genetics, 116, 541–545 (1987)), and was inserted into the BamHI site of *E. coli* plasmid pSP73 (Promega). The obtained plasmid was designated as pSP73-HUH.

Next, using pSP73-HUH as a template, a DNA fragment having a portion of the KRE2 gene added to both ends of the HUH cassette was amplified by PCR. The nucleotide sequence of the added KRE2 (SEQ ID NO: 41) gene was registered in the GenBank database under accession NO. X62647 (Hill et al., Genetics, 130, 273–283 (1992)), and the following primers were used: YF4 primer (TCATTGCAG-GTGCGGTTATTGTTCTCCTCCTAACAT-TGAAGATGAATTCGAGCTCGGTAC: SEQ ID NO: 26) wherein a region from +41 to +80 (underlined) of KRE2 (SEQ ID NO: 41) gene was added to the outside of hisG; and YR3 primer (TTTTTTCCAGTTTTTTGGCTTTACCAAC-CCTTGAGCATCATGCCTGCAGGTCGACTCTAG: SEQ ID NO: 27) wherein a region from +1317 to +1278 of KRE2 (SEQ ID NO: 41) gene was added thereto in the same manner. Using this PCR product (Δkre2::HUH), W303-1A (MATa leu2-3, 112 his3-11, 15 ade2-1 ura3–1 trp1-1 can1-

100) was transformed by the lithium acetate method (Ito et al., J. Bacteriol., 153, 163–168 (1983)). After transformation, the cells were plated to SD-Ura (2% glucose, 0.67% Yeast Nitrogen Base w/o amino acids (Difco), nucleobases excluding uracil, and amino acid mixture (20–400 mg/L)) medium containing 0.3 M KCl, and cultured at 30° C. for 2 days, thereby obtaining a transformant.

Genomic DNA was prepared from the transformant and the incorporation of a uracil marker into the KRE2 (SEQ ID NO: 41) region in a chromosome was confirmed by PCR using the above YF4 and YR3 primers. This transformant was designated as SSY3 strain.

From this strain, selection was carried out in YSD medium (1% yeast extract solution, 2% glucose, adenine (40 mg/L), uracil (20 mg/L)) containing 5-FOA, and URA3 gene deficient strain was obtained. In the same manner as described above, kre2 disrupted strain lacking URA3 gene was confirmed by PCR. This strain containing Δkre2::hisG was designated as SSY4 strain.

(2) Preparation of double disrupted strain retaining Δ kre2 Δ ktr1 marker and its properties The nucleotide sequence of KTR1 (SEQ ID NO: 42) gene is registered in the GenBank database under accession NO. X62941 (Hill et al., Genetics, 130, 273–283 (1992)). With the genomic DNA of W303-1A as a template, KTR1 (SEQ ID NO: 42) gene was amplified by PCR using YF5 primer (TGGTGCCTTCTTGCTTCTTTTTGC: SEQ ID NO: 28) encoding 5' untranslated region (−163 to −139) of KTR1 (SEQ ID NO: 42) gene and YR4 primer (GGTA-GAAAATATCAGTTGGGTTATC: SEQ ID NO: 29) encoding 3' untranslated region (+1372 to +1348) thereof. The obtained DNA fragment was inserted into SmaI site of pUC118 (Takara Shuzo) to prepare a plasmid pUC118-KTR1. This plasmid was cleaved at two BglII sites existing inside KTR1 (SEQ ID NO: 42), and then a HUH fragment obtained by cleaving pSP73-HUH at BglII-BamHI was inserted thereinto. The obtained plasmid was designated as pUC118-Δktr1::HUH. This plasmid was again amplified by PCR using the above YF5 and YR4 primers, and then using the obtained PCR fragment, SSY4 strain was transformed by lithium acetate method. After transformation, the cells were plated to SD-Ura medium containing 0.3 M KCl and cultured at 30° C. for 2 days, thereby obtaining a transformant.

Genomic DNA was prepared from the transformant and the incorporation of a uracil marker into the KTR1 (SEQ ID NO: 42) region in a chromosome was confirmed by PCR using the above YF5 and YR4 primers. This transformant was designated as SSY13 strain.

From this strain, selection was carried out in YSD medium containing 5-FOA, and URA3 gene deficient strain was obtained. In the same manner as described above, ktr1 disrupted strain lacking URA3 gene was confirmed by PCR. This strain containing (Δkre2::hisG,Δktr1::hisG) was designated as SSY14 strain.

(3) Preparation of Triple Disrupted Strain Retaining Δkre2Δktr1Δktr3 Marker

The nucleotide sequence of KTR3 (SEQ ID NO: 43) gene is registered in the GenBank database under accession NO. Z36074 (Feldmann et al., EMBO J., 13, 5795–5809 (1994)). With the genomic DNA of W303-1A as a template, KTR3 (SEQ ID NO: 43) gene was amplified by PCR using YF6 primer (TCGAAGAAAACAACGTAACTGATGG: SEQ ID NO: 30) encoding 5' untranslated region (−95 to −71) of ktr1 gene and YR5 primer (TTTTGCTTTTCTCTCT-TCATCTCCG: SEQ ID No: 31) encoding 3' untranslated region (+1385 to +1361) thereof. The obtained DNA fragment was inserted into SmaI site of pUC118 to prepare a plasmid pUC118-KTR3. This plasmid was cleaved at two EcoRV sites inside KTR3 (SEQ ID NO: 43), and then a HUH fragment which was obtained by cleaving pSP73-HUH at BglII-BamHI and blunted with Klenow Fragment, was inserted thereinto. The obtained plasmid was designated as pUC118-Δktr3::HUH. This plasmid was again amplified by PCR using the above YF6 and YR5 primers, and then using the obtained PCR fragment, SSY14 strain was transformed by lithium acetate method. After transformation, the cells were plated to SD-Ura medium containing 0.3 M KCl and cultured at 30° C. for 2 days, thereby obtaining a transformant.

Genomic DNA was prepared from the transformant and the incorporation of a uracil marker into the Δktr3 region in a chromosome was confirmed by PCR using the above YF6 and YR5 primers. This transformant was designated as SSY17 strain.

From this strain, selection was carried out in YSD medium containing 5-FOA and 0.3 M KCl, and a URA3 gene deficient strain was obtained. In the same manner as described above, URA3 gene-deficient ktr3 disrupted strain was confirmed by PCR. This strain containing (Δkre2::hisG, Δktr1::hisG,Δktr3::hisG) was designated as SSY18 strain.

Example 8

Expression of OMGnT Fusion Protein (VSV-G-Och1pTM-OMGnT) in Triple Disrupted Strain Retaining Δ kre2 Δ ktr1 Δ ktr3 Marker and Sugar Chain Structure Analysis of Mannoprotein on the Cell Surface (1) Construction of OMGnT Expression Vector (Chromosome Introducing Type) and Introduction Thereof into SSY18 Strain From YEp-OCH1-OMGnT prepared in Example 7, a region encoding VSV-G-Och1pTM-OMGnT and a region of a promoter and a terminator were excised with BamHI, and were inserted into the BamHI site of a chromosome-introducing type vector, pRS403 (HIS3 marker: STRATAGENE). The vector was cleaved at NheI inside HIS3 to be linearized. Using this DNA fragment, the transformation of the SSY18 strain was performed. In this transformation, the occurrence of homologous recombination with the HIS3 of a chromosome of the SSY18 strain enabled the introduction of one copy of the target gene into the chromosome. The transformation was performed by the method of Example 6, thereby obtaining a transformant. Genomic DNA was extracted from the transformant and the incorporation of the target gene into the genome was confirmed by PCR using YF7 primer (AAGTTGAGGGCTATGGAAGTGTATG: SEQ ID NO: 32) and YR6 primer (CACAAC-TAACTTTTTCCCGTTCCTC: SEQ ID NO: 33). The introduction of one copy of the gene at the HIS3 locus was confirmed by PCR using YF8 primer (GCTTTGCTGTGG-GAAAAACTTATCG: SEQ ID NO: 34) and the above YR6 primer. This transformant was designated as SSY11 strain.

(2) Introduction of Human UDP-GlcNAc Transporter (hUGTrel2) Gene

Sugar chains in glycoproteins of budding yeast are synthesized mainly from mannose, and it is considered that GlcNAc addition dose not take place in Golgi apparatus. Therefore, there was a possibility that UDP-GlcNAc, as a sugar donor to OMGnT, was of insufficient level in the Golgi apparatus. Thus, a human UDP-GlcNAc transporter gene (hUGTrel2) was introduced. This gene is known to transport UDP-GlcNAc from the cytoplasm to the Golgi apparatus in humans. The expression of hUGTrel2 in yeast has been reported by Ishida et al. (Ishida et al., J. Biochem., 126, 68–77 (1999)). With this expression vector as a template, UDP-GlcNAc transporter gene region was amplified by PCR using YF9 primer (AGAGCGGCCGCAAAATGT-TCGCCAACCTAA: SEQ ID NO: 35) and YR7 primer (TTTTGTCGACTAGACGCGTGAAGCATGCCC: SEQ ID NO: 36). After confirming the sequence of the amplified region, it was cleaved with NotI and SalI, and substituted with a site between NotI and SalI of an expression vector pG3-N (Chiba et al., Biochem. J., 308, 405–409 (1995)). Next, a UDP-GlcNAc transporter gene fragment including a promoter region was excised from this plasmid with NaeI and SmaI, and the excised fragment was inserted into the SmaI site of a chromosome introducing vector pRS404 (TRP1 marker; STRATAGENE). Thereafter, the vector was cleaved at BstXI inside TRP1, and linearlized. Using this DNA fragment, the transformation of the SSY11 strain was performed. The transformation was performed in accordance with Example 6, and a transformant was thereby obtained. Genomic DNA was extracted from the transformant, and the incorporation of the target gene into the genome was confirmed by PCR using YF10 primer (TTTGTGCCAACCAGTGTCTTTTTCC: SEQ ID NO: 37) and YR8 primer (TAAGTGCACTAGGGTCCGGT-TAAAC: SEQ ID NO: 38). The introduction of 1 copy of the gene at the HIS3 locus was confirmed by PCR using YF11 primer (ACGCGTATATTTCTACCAATCTCTC: SEQ ID NO: 39) and the above YR8 primer. This transformant was designated as SSY12 strain.

(3) Separation of Mannoprotein on Yeast Cell Surface and Structure Analysis of its O-Linked Man Type Sugar Chain The separation of mannoprotein on yeast cell surface was carried out based on a method by Chiba et al. (Chiba et al., J. Biol. Chem., 273, 26298–26304 (1998)), and the structure analysis of its O-linked Man type sugar chain was carried out based on a method by Iwase et al. (Iwase et al., Anal. Biochem., 206, 202–205 (1992)). Each type of yeast strain was placed into 150 ml of YPAD medium containing 0.3 M KCl, which was put into a 500-ml Sakaguchi flask, and cultured at 30° C. for 24 hours. Cells were collected by centrifugation and suspended in 2 ml of 20 mM sodium citrate buffer solution (pH 7.0), and the suspension was heated at 121° C. for 1 hour by an autoclave. After cooling, the suspension was centrifuged and a supernatant was collected. Another 2 ml of 20 mM sodium citrate buffer solution (pH 7.0) was added to the remaining solids and the mixture was heated and centrifuged in the same manner as above to further collect supernatants. All the extracts were combined and added to 3-times volume of ethanol. The resultant white precipitate was dried and then suspended in 1 ml of $H_2O$ and dialyzed against $H_2O$. Thereafter, the resultant was lyophilized, thereby obtaining mannoprotein.

Next, an O-linked type sugar chain was separated from the obtained mannoprotein by hydrazinolysis. The hydrazinolysis was performed using Hydraclub (Honen), and the procedure was carried out according to the manual. The decomposition conditions were 65° C. for 3 hours. After decomposition, the sugar chains were N-acetylated again, and then evaporated to dryness under a reduced pressure, thereby obtaining an O-linked type sugar chain preparation.

The obtained sugar chains were fluorescently labeled (pyridylamination, referred to as "PA"). Pyridylamination was performed using PAL Station (Takara Shuzo), and the procedure was carried out in accordance with the manual. After the reaction, the sugar chains were suspended in 500 μl of $H_2O$, thereby obtaining crude PA oligosaccharide preparation.

In order to remove unreacted 2-aminopyridine, 200 μl of aqueous ammonia was added to the crude sample, and an equivalent volume of phenol:chloroform (1:1) was further added thereto. After the mixture was vigorously shaken, an aqueous layer containing PA-oligosaccharide was collected. This procedure was repeated 7 times so that unreacted 2-aminopyridine was removed. The supernatant was filtered through a 0.22 μm filter, and thus, a PA-oligosaccharide preparation was obtained.

To confirm GlcNAc transfer to O-linked type sugar chains, the obtained PA-oligosaccharide preparation was digested with Jack bean β-N-acetylhexosaminidase (Seikagaku Corporation) and analyzed. 20 μl of PA-oligosaccharide preparation was evaporated to dryness under a reduced pressure, and then the resultant was suspended in 17.8 μl of $H_2O$. To the suspension, 0.2 μl of 1M NaOAc and 2 μl (20 mU) of HexNAc'ase were added and allowed to react at 37° C. overnight. The reaction was terminated by heating at 100° C. for 5 minutes, and the resultant was filtered through a 0.22 μm filter and analyzed by HPLC.

PA-oligosaccharide can be separated depending on the difference of chain length by HPLC using an amino column. SHODEX AsahiPak $NH_2P$-50 (4.6×250 mm, Showa Denko) was used as a column. A mixture solution (Solvent A) of 200 mM acetic acid-triethylamine buffer solution (pH 7.0) and acetonitrile (10:90) and a mixture solution (Solvent B) of 200 mM acetic acid-triethylamine buffer solution (pH 7.0) and acetonitrile (40:60) were used as solvents. The column was pre-equilibrated by running solvent A at a flow rate of 1.0 ml/min. Immediately after injection of the sample, the ratio of solvent B was linearly increased to 100% over a period of 60 minutes for the separation of PA-oligosaccharide.

The results of structure analysis of PA-oligosaccharide preparations prepared from OMGnT expression strains (SSY11 strain and SSY12 strain) and the parent strain are shown in FIG. 6 (A, C, and E). In the SSY11 strain and SSY12 strain, a clear peak of Man-GlcNAc was detected, while it was not recognized in the parent strain. Using Man-Man (M2) peak as a standard, SSY12 strain had a larger production of Man-GlcNAc than SSY11 strain. Further, when these preparations were digested with Jack bean β-N-acetylhexosamimidase, the peaks of Man-GlcNAc were remarkably decreased, indicating β linkage of GlcNAc (D and F of FIG. 6). In consideration of these results and enzymatic properties of OMGnT as mentioned in Example 4, it can be said that O-linked Man type sugar chains in yeast cell wall can be converted to mammalian type GlcNAcβ1→2Man structure by expressing OMGnT.

INDUSTRIAL APPLICABILITY

According to the present invention, the following are provided: a novel N-acetylglucosaminyltransferase (OMGnT), its solubilized enzyme, and an activity assay method and production method thereof, and a polynucleotide encoding the enzyme. With the OMGnT of the present invention, it has become possible to produce complex carbohydrates which could not be formed with conventional glycosyltransferases. Thus, the OMGnT of the present invention is useful for modifying and analyzing sugar chain structures on the surface of any biopolymer as well as for producing and improving complex carbohydrate type pharmaceuticals, reagents, and foods.

The polynucleotide encoding the OMGnT of the present invention is useful for the diagnosis or treatment of diseases such as nervous diseases and morphological abnormalities, and for the modification of sugar chain structures of complex carbohydrate products using microorganisms, animals or the like.

Further, antibodies and antiserum obtained by using the OMGnT protein of the present invention as an antigen, or a part or all of the polynucleotide encoding the OMGnT of the present invention can be used as a probe for the characterization of various animal tissues, blood, blood cell components, cultured cells, and microorganisms, and thus useful for the detection and diagnosis of diseases such as nervous diseases and morphological abnormalities.

Sequence listing free text
SEQ ID NO: 3—Description of Artificial Sequence: primer
SEQ ID NO: 4—Description of Artificial Sequence: primer
SEQ ID NO: 5—Description of Artificial Sequence: primer
SEQ ID NO: 6—Description of Artificial Sequence: primer
SEQ ID NO: 7—Description of Artificial Sequence: primer
SEQ ID NO: 8—Description of Artificial Sequence: primer
SEQ ID NO: 9—Description of Artificial Sequence: primer
SEQ ID NO: 10—Description of Artificial Sequence: primer
SEQ ID NO: 11—Description of Artificial Sequence: primer
SEQ ID NO: 12—Description of Artificial Sequence: primer
SEQ ID NO: 13—Description of Artificial Sequence: primer
SEQ ID NO: 14—Description of Artificial Sequence: primer
SEQ ID NO: 15—Description of Artificial Sequence: primer
SEQ ID NO: 16—Description of Artificial Sequence: primer
SEQ ID NO: 17—Description of Artificial Sequence: primer
SEQ ID NO: 18—Description of Artificial Sequence: primer
SEQ ID NO: 19—Description of Artificial Sequence: primer
SEQ ID NO: 20—Description of Artificial Sequence: primer
SEQ ID NO: 21—Description of Artificial Sequence: primer
SEQ ID NO: 22—Description of Artificial Sequence: primer
SEQ ID NO: 23—Description of Artificial Sequence: primer
SEQ ID NO: 24—Description of Artificial Sequence: primer
SEQ ID NO: 25—Description of Artificial Sequence: primer
SEQ ID NO: 26—Description of Artificial Sequence: primer
SEQ ID NO: 27—Description of Artificial Sequence: primer
SEQ ID NO: 28—Description of Artificial Sequence: primer
SEQ ID NO: 29—Description of Artificial Sequence: primer
SEQ ID NO: 30—Description of Artificial Sequence: primer
SEQ ID NO: 31—Description of Artificial Sequence: primer
SEQ ID NO: 32—Description of Artificial Sequence: primer
SEQ ID NO: 33—Description of Artificial Sequence: primer
SEQ ID NO: 34—Description of Artificial Sequence: primer
SEQ ID NO: 35—Description of Artificial Sequence: primer
SEQ ID NO: 36—Description of Artificial Sequence: primer
SEQ ID NO: 37—Description of Artificial Sequence: primer
SEQ ID NO: 38—Description of Artificial Sequence: primer
SEQ ID NO: 39—Description of Artificial Sequence: primer Many references are cited herein to describe the present invention, and they are incorporated herein by reference in their entirety.

What is claimed is:

1. An isolated polynucleotide encoding N-acetylglucosaminyltransferase comprising the nucleotide sequence of SEQ ID NO: 1.

2. A recombinant polynucleotide obtained by insertion of the polynucleotide encoding N-acetylglucasaminyltransferase according to claim 1 into a vector.

3. An isolated host cell comprising said recombinant polynucleotide according to claim 2.

4. A yeast cell comprising said recombinant polynucleotide according to claim 2 and having at least one of KRE2 SEQ ID NO: 41, KTR1 SEQ ID NO: 42, and KTR3 SEQ ID NO: 43 genes disrupted.

5. A yeast cell comprising the recombinant polynucleotide according to claim 2 and being a triple disrupted strain wherein KRE2 SEQ ID NO: 41, KTR1 SEQ ID NO: 42, and KTR3 SEQ ID NO: 43 genes are disrupted.

6. A method for producing a protein having N-acetylglucosaminyltransferase activity encoded by the nucleotide sequence of SEQ ID NO: 1, comprising the step of collecting said protein from a biological sample, wherein: (i) said biological sample comprises host cells in a medium, which host cells respectively express said nucleotide sequence of SEQ ID NO: 1; end (ii) said protein is collected from said host cells or from said medium.

7. A method according to claim 6, wherein said host cell is a yeast cell in which at least one of KRE2 SEQ ID NO: 41, KTR1 SEQ ID NO: 42, and KTR3 SEQ ID NO: 43 genes is disrupted.

8. A method according to claim 7, wherein all of said genes are disrupted.

* * * * *

SEQUENCE LISTING

```
<160> NUMBER OF SEQ ID NOS: 40

<210> SEQ ID NO 1
<211> LENGTH: 2393
<212> TYPE: DNA
<213> ORGANISM: Homo sapiens
<220> FEATURE:
<221> NAME/KEY: CDS
<222> LOCATION: (95)..(2074)

<400> SEQUENCE: 1 gagggccta gcggggcccg agcggggccc ggggccccta agccattcct gaagtcatgg      60
gctggccagg acattggtga cccgccaatc cggt atg gac gac tgg aag ccc agc    115
                                    Met Asp Asp Trp Lys Pro Ser
                                     1               5 ccc ctc atc aag ccc ttt ggg gct cgg aag aag cgg agc tgg tac ctt      163
Pro Leu Ile Lys Pro Phe Gly Ala Arg Lys Lys Arg Ser Trp Tyr Leu
         10                  15                  20 acc tgg aag tat aaa ctg aca aac cag cgg gcc ctg cgg aga ttc tgt      211
Thr Trp Lys Tyr Lys Leu Thr Asn Gln Arg Ala Leu Arg Arg Phe Cys
     25                  30                  35 cag aca ggg gcc gtg ctt ttc ctg ctg gtg act gtc att gtc aat atc      259
Gln Thr Gly Ala Val Leu Phe Leu Leu Val Thr Val Ile Val Asn Ile
 40                  45                  50                  55 aag ttg atc ctg gac act cgg cga gcc atc agt gaa gcc aat gaa gac      307
Lys Leu Ile Leu Asp Thr Arg Arg Ala Ile Ser Glu Ala Asn Glu Asp
                 60                  65                  70 cca gag cca gag caa gac tat gat gag gcc cta ggc cgc ctg gag ccc      355
Pro Glu Pro Glu Gln Asp Tyr Asp Glu Ala Leu Gly Arg Leu Glu Pro
             75                  80                  85 cca cgg cgc aga ggc agt ggt ccc cgg cgg gtc ctg gac gta gag gtg      403
```

```
Pro Arg Arg Arg Gly Ser Gly Pro Arg Arg Val Leu Asp Val Glu Val
         90              95              100 tat tca agt cgc agc aaa gta tat gtg gca gtg gat ggc acc acg gtg    451
Tyr Ser Ser Arg Ser Lys Val Tyr Val Ala Val Asp Gly Thr Thr Val
105             110             115 ctg gag gat gag gcc cgg gag cag ggc cgg ggc atc cat gtc att gtc    499
Leu Glu Asp Glu Ala Arg Glu Gln Gly Arg Gly Ile His Val Ile Val
120             125             130             135 ctc aac cag gcc acg ggc cac gtg atg gca aaa cgt gtg ttt gac acg    547
Leu Asn Gln Ala Thr Gly His Val Met Ala Lys Arg Val Phe Asp Thr
                140             145             150 tac tca cct cat gag gat gag gcc atg gtg cta ttc ctc aac atg gta    595
Tyr Ser Pro His Glu Asp Glu Ala Met Val Leu Phe Leu Asn Met Val
            155             160             165 gcg ccc ggc cga gtg ctc atc tgc act gtc aag gat gag ggc tcc ttc    643
Ala Pro Gly Arg Val Leu Ile Cys Thr Val Lys Asp Glu Gly Ser Phe
        170             175             180 cac ctc aag gac aca gcc aag gct ctg ctg agg agc ctg ggc agc cag    691
His Leu Lys Asp Thr Ala Lys Ala Leu Leu Arg Ser Leu Gly Ser Gln
185             190             195 gct ggc cct gcc ctg ggc tgg agg gac aca tgg gcc ttc gtg gga cga    739
Ala Gly Pro Ala Leu Gly Trp Arg Asp Thr Trp Ala Phe Val Gly Arg
200             205             210             215 aaa gga ggt cct gtc ttc ggg gag aaa cat tct aaa tca cct gcc ctc    787
Lys Gly Gly Pro Val Phe Gly Glu Lys His Ser Lys Ser Pro Ala Leu
                220             225             230 tct tcc tgg ggg gac cca gtc ctg ctg aag aca gat gtg cca ttg agc    835
Ser Ser Trp Gly Asp Pro Val Leu Leu Lys Thr Asp Val Pro Leu Ser
            235             240             245 tca gca gaa gag gca gag tgc cac tgg gca gac aca gag ctg aac cgt    883
Ser Ala Glu Glu Ala Glu Cys His Trp Ala Asp Thr Glu Leu Asn Arg
        250             255             260 cgc cgc cgg cgc ttc tgc agc aaa gtt gag ggc tat gga agt gta tgc    931
Arg Arg Arg Arg Phe Cys Ser Lys Val Glu Gly Tyr Gly Ser Val Cys
265             270             275 agc tgc aag gac ccc aca ccc atc gag ttc agc cct gac cca ctc cca    979
Ser Cys Lys Asp Pro Thr Pro Ile Glu Phe Ser Pro Asp Pro Leu Pro
280             285             290             295 gac aac aag gtc ctc aat gtg cct gtg gct gtc att gca ggg aac cga    1027
Asp Asn Lys Val Leu Asn Val Pro Val Ala Val Ile Ala Gly Asn Arg
                300             305             310 ccc aat tac ctg tac agg atg ctg cgc tct ctg ctt tca gcc cag ggg    1075
Pro Asn Tyr Leu Tyr Arg Met Leu Arg Ser Leu Leu Ser Ala Gln Gly
            315             320             325 gtg tct cct cag atg ata aca gtt ttc att gac ggc tac tat gag gaa    1123
Val Ser Pro Gln Met Ile Thr Val Phe Ile Asp Gly Tyr Tyr Glu Glu
        330             335             340 ccc atg gat gtg gtg gca ctg ttt ggt ctg agg ggc atc cag cat act    1171
Pro Met Asp Val Val Ala Leu Phe Gly Leu Arg Gly Ile Gln His Thr
345             350             355 ccc atc agc atc aag aat gcc cgc gtg tct cag cac tac aag gcc agc    1219
Pro Ile Ser Ile Lys Asn Ala Arg Val Ser Gln His Tyr Lys Ala Ser
360             365             370             375 ctc act gcc act ttc aac ctg ttt ccg gag gcc aag ttt gct gtg gtt    1267
Leu Thr Ala Thr Phe Asn Leu Phe Pro Glu Ala Lys Phe Ala Val Val
                380             385             390 ctg gaa gag gac ctg gac att gct gtg gat ttt ttc agt ttc ctg agc    1315
Leu Glu Glu Asp Leu Asp Ile Ala Val Asp Phe Phe Ser Phe Leu Ser
            395             400             405
```

```
caa tcc atc cac cta ctg gag gag gat gac agc ctg tac tgc atc tct    1363
Gln Ser Ile His Leu Leu Glu Glu Asp Asp Ser Leu Tyr Cys Ile Ser
        410                 415                 420 gcc tgg aat gac cag ggg tat gaa cac acg gct gag gac cca gca cta    1411
Ala Trp Asn Asp Gln Gly Tyr Glu His Thr Ala Glu Asp Pro Ala Leu
425                 430                 435 ctg tac cgt gtg gag acc atg cct ggg ctg ggc tgg gtg ctc agg agg    1459
Leu Tyr Arg Val Glu Thr Met Pro Gly Leu Gly Trp Val Leu Arg Arg
440                 445                 450                 455 tcc ttg tac aag gag gag ctt gag ccc aag tgg cct aca ccg gaa aag    1507
Ser Leu Tyr Lys Glu Glu Leu Glu Pro Lys Trp Pro Thr Pro Glu Lys
                460                 465                 470 ctc tgg gat tgg gac atg tgg atg cgg atg cct gaa caa cgc cgg ggc    1555
Leu Trp Asp Trp Asp Met Trp Met Arg Met Pro Glu Gln Arg Arg Gly
            475                 480                 485 cga gag tgc atc atc cct gac gtt tcc cga tcc tac cac ttt ggc atc    1603
Arg Glu Cys Ile Ile Pro Asp Val Ser Arg Ser Tyr His Phe Gly Ile
        490                 495                 500 gtc ggc ctc aac atg aat ggc tac ttt cac gag gcc tac ttc aag aag    1651
Val Gly Leu Asn Met Asn Gly Tyr Phe His Glu Ala Tyr Phe Lys Lys
505                 510                 515 cac aag ttc aac acg gtt cca ggt gtc cag ctc agg aat gtg gac agt    1699
His Lys Phe Asn Thr Val Pro Gly Val Gln Leu Arg Asn Val Asp Ser
520                 525                 530                 535 ctg aag aaa gaa gct tat gaa gtg gaa gtt cac agg ctg ctc agt gag    1747
Leu Lys Lys Glu Ala Tyr Glu Val Glu Val His Arg Leu Leu Ser Glu
                540                 545                 550 gct gag gtt ctg gac cac agc aag aac cct tgt gaa gac tct ttc ctg    1795
Ala Glu Val Leu Asp His Ser Lys Asn Pro Cys Glu Asp Ser Phe Leu
            555                 560                 565 cca gac aca gag ggc cac acc tac gtg gcc ttt att cga atg gag aaa    1843
Pro Asp Thr Glu Gly His Thr Tyr Val Ala Phe Ile Arg Met Glu Lys
        570                 575                 580 gat gat gac ttc acc acc tgg acc cag ctt gcc aag tgc ctc cat atc    1891
Asp Asp Asp Phe Thr Thr Trp Thr Gln Leu Ala Lys Cys Leu His Ile
585                 590                 595 tgg gac ctg gat gtg cgt ggc aac cat cgg ggc ctg tgg aga ttg ttt    1939
Trp Asp Leu Asp Val Arg Gly Asn His Arg Gly Leu Trp Arg Leu Phe
600                 605                 610                 615 cgg aag aag aac cac ttc ctg gtg gtg ggg gtc ccg gct tcc ccc tac    1987
Arg Lys Lys Asn His Phe Leu Val Val Gly Val Pro Ala Ser Pro Tyr
                620                 625                 630 tca gtg aag aag cca ccc tca gtc acc cca att ttc ctg gag cca ccc    2035
Ser Val Lys Lys Pro Pro Ser Val Thr Pro Ile Phe Leu Glu Pro Pro
            635                 640                 645 cca aag gag gag gga gcc cca gga gcc cca gaa cag aca tgagacctcc    2084
Pro Lys Glu Glu Gly Ala Pro Gly Ala Pro Glu Gln Thr
        650                 655                 660 tccaggaccc tgcgggctgg gtactgtgta cccccaggct ggctagccct tccctccatc    2144
ctgtaggatt tgtagatgc tggtagggc tgggctacc ttgttttta catgagactt        2204 aattactaac tccaagggga gggttcccct gctccaacac cccgttcctg agttaaaagt    2264
ctatttattt acttccttgt tggagaaggg caggagagta cctgggaatc attacgatcc    2324
ctagcagctc atcctgccct ttgaataccc tcactttcca ggcctggctc agaatctaac    2384
ctatttatt                                                            2393

<210> SEQ ID NO 2
<211> LENGTH: 660
```

```
<212> TYPE: PRT
<213> ORGANISM: Homo sapiens

<400> SEQUENCE: 2

Met Asp Asp Trp Lys Pro Ser Pro Leu Ile Lys Pro Phe Gly Ala Arg
 1               5                  10                  15

Lys Lys Arg Ser Trp Tyr Leu Thr Trp Lys Tyr Lys Leu Thr Asn Gln
            20                  25                  30

Arg Ala Leu Arg Arg Phe Cys Gln Thr Gly Ala Val Leu Phe Leu Leu
        35                  40                  45

Val Thr Val Ile Val Asn Ile Lys Leu Ile Leu Asp Thr Arg Arg Ala
50                  55                  60

Ile Ser Glu Ala Asn Glu Asp Pro Glu Pro Glu Gln Asp Tyr Asp Glu
65                  70                  75                  80

Ala Leu Gly Arg Leu Glu Pro Pro Arg Arg Arg Gly Ser Gly Pro Arg
                85                  90                  95

Arg Val Leu Asp Val Glu Val Tyr Ser Ser Arg Ser Lys Val Tyr Val
            100                 105                 110

Ala Val Asp Gly Thr Thr Val Leu Glu Asp Glu Ala Arg Glu Gln Gly
        115                 120                 125

Arg Gly Ile His Val Ile Val Leu Asn Gln Ala Thr Gly His Val Met
    130                 135                 140

Ala Lys Arg Val Phe Asp Thr Tyr Ser Pro His Glu Asp Glu Ala Met
145                 150                 155                 160

Val Leu Phe Leu Asn Met Val Ala Pro Gly Arg Val Leu Ile Cys Thr
                165                 170                 175

Val Lys Asp Glu Gly Ser Phe His Leu Lys Asp Thr Ala Lys Ala Leu
            180                 185                 190

Leu Arg Ser Leu Gly Ser Gln Ala Gly Pro Ala Leu Gly Trp Arg Asp
        195                 200                 205

Thr Trp Ala Phe Val Gly Arg Lys Gly Gly Pro Val Phe Gly Glu Lys
210                 215                 220

His Ser Lys Ser Pro Ala Leu Ser Ser Trp Gly Asp Pro Val Leu Leu
225                 230                 235                 240

Lys Thr Asp Val Pro Leu Ser Ser Ala Glu Glu Ala Glu Cys His Trp
                245                 250                 255

Ala Asp Thr Glu Leu Asn Arg Arg Arg Arg Phe Cys Ser Lys Val
            260                 265                 270

Glu Gly Tyr Gly Ser Val Cys Ser Cys Lys Asp Pro Thr Pro Ile Glu
        275                 280                 285

Phe Ser Pro Asp Pro Leu Pro Asp Asn Lys Val Leu Asn Val Pro Val
    290                 295                 300

Ala Val Ile Ala Gly Asn Arg Pro Asn Tyr Leu Tyr Arg Met Leu Arg
305                 310                 315                 320

Ser Leu Leu Ser Ala Gln Gly Val Ser Pro Gln Met Ile Thr Val Phe
                325                 330                 335

Ile Asp Gly Tyr Tyr Glu Glu Pro Met Asp Val Val Ala Leu Phe Gly
            340                 345                 350

Leu Arg Gly Ile Gln His Thr Pro Ile Ser Ile Lys Asn Ala Arg Val
        355                 360                 365

Ser Gln His Tyr Lys Ala Ser Leu Thr Ala Thr Phe Asn Leu Phe Pro
    370                 375                 380

Glu Ala Lys Phe Ala Val Val Leu Glu Glu Asp Leu Asp Ile Ala Val
385                 390                 395                 400
```

```
Asp Phe Phe Ser Phe Leu Ser Gln Ser Ile His Leu Glu Glu Asp
                405                 410                 415
Asp Ser Leu Tyr Cys Ile Ser Ala Trp Asn Asp Gln Gly Tyr Glu His
            420                 425                 430
Thr Ala Glu Asp Pro Ala Leu Leu Tyr Arg Val Glu Thr Met Pro Gly
        435                 440                 445
Leu Gly Trp Val Leu Arg Arg Ser Leu Tyr Lys Glu Leu Glu Pro
    450                 455                 460
Lys Trp Pro Thr Pro Glu Lys Leu Trp Asp Trp Asp Met Trp Met Arg
465                 470                 475                 480
Met Pro Glu Gln Arg Arg Gly Arg Glu Cys Ile Ile Pro Asp Val Ser
                485                 490                 495
Arg Ser Tyr His Phe Gly Ile Val Gly Leu Asn Met Asn Gly Tyr Phe
            500                 505                 510
His Glu Ala Tyr Phe Lys Lys His Lys Phe Asn Thr Val Pro Gly Val
        515                 520                 525
Gln Leu Arg Asn Val Asp Ser Leu Lys Lys Glu Ala Tyr Glu Val Glu
    530                 535                 540
Val His Arg Leu Leu Ser Glu Ala Glu Val Leu Asp His Ser Lys Asn
545                 550                 555                 560
Pro Cys Glu Asp Ser Phe Leu Pro Asp Thr Glu Gly His Thr Tyr Val
                565                 570                 575
Ala Phe Ile Arg Met Glu Lys Asp Asp Phe Thr Thr Trp Thr Gln
            580                 585                 590
Leu Ala Lys Cys Leu His Ile Trp Asp Leu Asp Val Arg Gly Asn His
    595                 600                 605
Arg Gly Leu Trp Arg Leu Phe Arg Lys Lys Asn His Phe Leu Val Val
    610                 615                 620
Gly Val Pro Ala Ser Pro Tyr Ser Val Lys Lys Pro Pro Ser Val Thr
625                 630                 635                 640
Pro Ile Phe Leu Glu Pro Pro Lys Glu Glu Gly Ala Pro Gly Ala
                645                 650                 655
Pro Glu Gln Thr
            660

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 3
gaccagtcct gctgaagaca gat                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 4
ggtccaggtg gtgaagtcat cat                                              23

<210> SEQ ID NO 5
<211> LENGTH: 23
```

```
<212> TYPE: DNA
<213> ORGANISM: Artificial Sequence
<220> FEATURE:
<223> OTHER INFORMATION: Description of Artificial Sequence: Primer

<400> SEQUENCE: 5
ccagctcagg aatgtggaca gtc                                             23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
ttcaaggccc tcaggacagt c                                               21

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
ccatcctaat acgactcact atagggc                                         27

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
gctgagctca atggcacatc tg                                              22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 9
actcactata gggctcgagc ggc                                             23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
ttgacgcaaa tgggcggtag gc                                              22

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
```

-continued gagaaccccc ggccggctgg gccgcgtcac                                               30

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 12
ccagccggcc gggggttctc atcatcatca t                                             31

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
tagaaggcac agtcgaggct g                                                        21

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 14
aaggatcctc agcagaagag gcagagtgc                                                29

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 15
ttctcgaggg tcctggagga ggtctcat                                                 28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16
gcggatccag tgaagccaat gaagacccag                                               30

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 17
gcagctgcat acacttccat agc                                                      23

<210> SEQ ID NO 18
<211> LENGTH: 30
<212> TYPE: DNA
<213> ORGANISM: Artificial Sequence

```
<220> FEATURE:
<223> OTHER INFORMATION: Description of Artificial Sequence: Primer

<400> SEQUENCE: 18
caggatccgt cagcgctctc gatggcgacc                              30

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 19
ctcctcgagg aaggacaggc aggtgctaa                               29

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
tttgctagcc aatccggtat ggacgactgg                              30

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 21
tgaatagatt gggtaagatg gacgactgga agccc                        35

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 22
cccagtggca ctctgcctct tctgc                                   25

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 23
cccgaattca tgtacactga tattgaaatg aatagattgg gtaag             45

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 24
tgaatagatt gggtaagatg tctaggaagt tgtccc                       36
```

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 25
ggggagctca aatttatatc ttgtg                                  25

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 26
tcattgcagg tgcggttatt gttctcctcc taacattgaa gatgaattcg agctcggtac   60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 27 tttttttccag ttttttggct ttaccaaccc ttgagcatca tgcctgcagg tcgactctag   60

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 28
tggtgccttc ttgcttcttt tttgc                                  25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 29
ggtagaaaat atcagttggg ttatc                                  25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
tcgaagaaaa caacgtaact gatgg                                  25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 31
ttttgctttt ctctcttcat ctccg    25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 32
aagttgaggg ctatggaagt gtatg    25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 33
cacaactaac tttttcccgt tcctc    25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 34
gctttgctgt gggaaaaact tatcg    25

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 35
agagcggccg caaaatgttc gccaacctaa    30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 36
ttttgtcgac tagacgcgtg aagcatgccc    30

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 37
tttgtgccaa ccagtgtctt tttcc    25

<210> SEQ ID NO 38

```
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 38
taagtgcact agggtccggt taaac                                    25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 39
acgcgtatat ttctaccaat ctctc                                    25

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 40

Ala Ala Pro Thr Pro Val Ala Ala Pro
 1               5
```